US010092614B2

(12) United States Patent
Potvin et al.

(10) Patent No.: US 10,092,614 B2
(45) Date of Patent: Oct. 9, 2018

(54) NUTRIPROTECTIVE DIET

(75) Inventors: Steeves Potvin, Quebec (CA); Vincent Bédard, Quebec (CA); François Béland, L'Ancienne-Lorette (CA); Geneviève Béland, St-Hyacinthe (CA); Keiko Abe, Saitama (JP)

(73) Assignee: FÉDÉRATION DES PRODUCTEURS ACÉRICOLES DU QUÉBEC, Québec (CA)

( * ) Notice: Subject to any disclaimer, the term of this patent is extended or adjusted under 35 U.S.C. 154(b) by 0 days.

(21) Appl. No.: 14/344,319

(22) PCT Filed: Sep. 10, 2012

(86) PCT No.: PCT/CA2012/000832
§ 371 (c)(1),
(2), (4) Date: Oct. 13, 2014

(87) PCT Pub. No.: WO2013/033828
PCT Pub. Date: Mar. 14, 2013

(65) Prior Publication Data
US 2015/0140143 A1    May 21, 2015

Related U.S. Application Data

(60) Provisional application No. 61/532,808, filed on Sep. 9, 2011.

(51) Int. Cl.
| | | |
|---|---|---|
| A61K 36/00 | (2006.01) | |
| A61K 36/77 | (2006.01) | |
| A23L 5/00 | (2016.01) | |
| A23L 33/125 | (2016.01) | |
| A61K 36/88 | (2006.01) | |
| A61K 36/889 | (2006.01) | |
| A61K 36/899 | (2006.01) | |
| A61K 36/185 | (2006.01) | |
| A61K 36/20 | (2006.01) | |
| A61K 9/00 | (2006.01) | |
| A23L 29/30 | (2016.01) | |
| A23L 33/00 | (2016.01) | |
| A23L 33/10 | (2016.01) | |
| A23L 33/105 | (2016.01) | |

(52) U.S. Cl.
CPC ........... *A61K 36/77* (2013.01); *A23L 5/00* (2016.08); *A23L 29/30* (2016.08); *A23L 33/10* (2016.08); *A23L 33/105* (2016.08); *A23L 33/125* (2016.08); *A23L 33/30* (2016.08); *A61K 9/0095* (2013.01); *A61K 36/185* (2013.01); *A61K 36/20* (2013.01); *A61K 36/88* (2013.01); *A61K 36/889* (2013.01); *A61K 36/899* (2013.01); *A61K 2236/30* (2013.01)

(58) Field of Classification Search
CPC .................................................... A61K 36/00
USPC ........................................................ 424/725
See application file for complete search history.

(56) References Cited

U.S. PATENT DOCUMENTS

| | | | | |
|---|---|---|---|---|
| 3,362,833 | A | * | 1/1968 | Smith ............... A23L 1/053 426/658 |
| 4,006,032 | A | * | 2/1977 | Hills ............... A23L 29/30 127/46.2 |
| 2008/0026114 | A1 | * | 1/2008 | Johnson ............ B65D 81/3453 426/114 |
| 2009/0117056 | A1 | | 5/2009 | Hodal, Jr. et al. |
| 2010/0159082 | A1 | * | 6/2010 | Rupasinghe ......... A23B 7/0053 426/102 |
| 2013/0267474 | A1 | * | 10/2013 | Seeram ............. A61K 31/09 514/25 |
| 2013/0310332 | A1 | * | 11/2013 | Barbeau ............ A23F 3/34 514/35 |

FOREIGN PATENT DOCUMENTS

| | | | |
|---|---|---|---|
| AU | A-74105/96 | * | 2/1996 |
| CA | 1062953 | * | 9/1979 |
| CA | 1081530 | * | 7/1980 |
| CA | 2600091 | * | 2/2009 |
| WO | 2010/099617 A1 | | 9/2010 |
| WO | WO-2012/021981 A1 | | 2/2012 |
| WO | WO-2012/021983 A1 | | 2/2012 |
| WO | WO-2012/055010 A1 | | 5/2012 |

OTHER PUBLICATIONS

Di Mauro et al., J. Agric. Food Chem, 1999, 47, 4391-4397.*
Jensen et al., American Journal of Enology and Viticulture, 58(4), 451-460, 2007.*
Abe et al. (2011). "Analyzing the physiological functionalities of maple syrup from Canada." Abstract. 1 page.
Zhang et al. (2014). "Chemical Compositional, Biological, and Safety Studies of a Novel Maple Syrup Derived Extract for Nutraceutical Applications." *J. Agric. Food Chem.* 62, 6687-6698.
Deslauriers, Isabelle, "Recovery, Separation and Characterization of Phenolic Compounds and Flavonoids from Maple Products", A Thesis Submitted to the Faculty of Graduate Studies and Research in Partial Fulfillment of the Requirement of the Degree of Master of Science, McGill University, 2000, 120 pages.

(Continued)

*Primary Examiner* — Michael V Meller
(74) *Attorney, Agent, or Firm* — Morrison & Foerster LLP

(57) ABSTRACT

The present document describes a nutriprotective diet comprising a nutriprotective amount of a sugar plant syrup, a sugar plant syrup extract, a sugar plant extract, or combinations thereof The present document also describes a method of eliciting a nutriprotective effect in a subject, which comprises administering a nutriprotective amount of a nutriprotective diet according to the present invention. Also, the present document also describes a method of treating a subject with a disorder, by administering a nutriprotective amount of a nutriprotective diet according to the present invention. Also, the present document describes a process for the extraction of polyphenolic compounds from maple syrup using adsorbent materials, and the extracts obtained therefrom.

1 Claim, 31 Drawing Sheets

(56) References Cited

OTHER PUBLICATIONS

Favati et al., "Rapid Determination of Phenol Content in Extra Virgin Olive Oil", Grasas y Aceites, vol. 45, No. 1-2, 1994, pp. 68-70.

Lawler-Neville et al., "Effects of Concentrated Separator by-Product(Desugared Molasses) on Intake, Site of Digestion, Microbial Efficiency, and Nitrogen Balance in Ruminants Fed Forage-Based Diets", Journal of Animal Science, vol. 84, 2006, pp. 2232-2242.

Mackie et al., "Changes in Lactate-Producing and Lactate-Utilizing Bacteria in Relation to pH in the Rumen of Sheep During Stepwise Adaptation to a High-Concentrate Diet", Applied and Environmental Microbiology, vol. 38, No. 3, Sep. 1979, pp. 422-430.

International Preliminary Report on Patentability received for PCT Patent Application No. PCT/CA2012/000832, completed on Jan. 7, 2014, 14 pages.

International Search Report & Written Opinion received for PCT Patent Application No. PCT/CA2012/000832, dated Jan. 9, 2013, 7 pages.

University of Rhode Island, "54 Beneficial Compounds Discovered in Pure Maple Syrup", Science News, Mar. 30, 2011, 4 pages.

Watanabe et al., "Ingested Maple Syrup Evokes a Possible Liver-Protecting Effect Physiologic and Genomic Investigations with Rats", Bioscience, Biotechnology, and Biochemistry, vol. 75, No. 12, 2011, pp. 2408-2410.

Yamauchi et al., "Histological Intestinal Recovery in Chickens Refed Dietary Sugar Cane Extract", Poultry Science, vol. 85, 2006, pp. 645-651.

\* cited by examiner

NUTRIPROTECTIVE DIET

CROSS-REFERENCE TO RELATED APPLICATIONS

This application is a U.S. national phase of International Application under 35 USC § 371 of PCT/CA2012/000832, filed Sep. 10, 2012, which claims priority from and the benefit under 35 USC 119(e) of U.S. provisional patent application 61/532,808, filed on Sep. 9, 2011, the specification of which is hereby incorporated by reference, in its entirety.

BACKGROUND (a) Field

The present document describes a nutriprotective diet comprising a nutriprotective amount of a sugar plant syrup, a sugar plant syrup extract, a sugar plant extract, a rejection of a sugar plant extract, or combinations thereof. The present document also describes a method of eliciting a nutriprotective effect in a subject, which comprises administering a nutriprotective amount of a nutriprotective diet according to the present invention. Also, the present document also describes a method of treating a subject with a disorder, by administering a nutriprotective amount of a nutriprotective diet according to the present invention. Also, the present document describes a process for the extraction of polyphenolic compounds from maple syrup using adsorbent materials, and the extracts obtained therefrom.

(b) Related Prior Art

Maple syrup (MS), a natural sweetener consumed as a palatable sweetener, is obtained by concentrating the sap collected from certain maple species including the sugar maple (*Acer saccharum*), which is native to North America. It is a very popular food product preferred by a large number of children, adults and even elderly people in the world.

With the realization that diets and lifestyle of different populations may determine their rates of cancer and other diseases, more and more individuals try to increase their intake in natural products such as MS with the expectation that it may also be good for their health.

Hepatic diseases or hepatic dysfunction are known to be closely involved in all life-style related diseases such as diabetes mellitus. In addition, decreased hepatic function is pointed out as a major cause of aging. In a modern era in which people are exposed to many factors that increase active oxygen species harmful to organs such as tobacco, alcohol, high-fat diet and stress, it can be said that people live in an environment that tends to damage hepatic function. Daily diet is an important key to prevent life-style related diseases including metabolic syndrome. Continuous intake of foods with liver-protecting function may be promising for their prevention.

Liver diseases are classified according to their cause into viral liver diseases, alcoholic liver diseases, liver diseases by drug toxicity, fatty liver diseases, autoimmune liver diseases, metabolic liver diseases and other liver diseases. Liver diseases are difficult to diagnose in early stages owing to the absence of subjective symptoms, and thus are the leading causes of death in many countries. However, there is still no effective therapeutic agent and diagnostic method for liver diseases.

Many studies on the use of natural materials for the prevention and treatment of liver diseases have been conducted. Typical examples of such natural materials include silymarin isolated from the seeds of *Silybum marianum*, gomisin isolated from *Schizandra chinensis*, glycyrrhizin isolated from licorice root, and the like. However, none relate to the use of MS.

The liver being the chemical factory of the human body, it is directly affected by our food-intake. Considering the world-wide popularity of MS, and the fact there is no scientific evidence available regarding the health-promoting effect of a maple syrup-containing diet, increased knowledge of the function of MS would aid in the prevention of lifestyle-related diseases such as liver diseases.

SUMMARY

According to an embodiment, there is provided a nutriprotective diet comprising a nutriprotective amount of a sugar plant syrup, a sugar plant syrup extract, a sugar plant extract, a rejection of a plant extract, or combinations thereof The nutriprotective amount of sugar plant syrup may be at least 1% sugar plant syrup up to 99% sugar plant syrup.

The nutriprotective amount of sugar plant syrup may be at least 10% sugar plant syrup up to 70%% sugar plant syrup.

The nutriprotective amount of sugar plant syrup may be 20% sugar plant syrup.

The nutriprotective amount of a sugar plant syrup extract may be from about 0.0010% to about 0.15% of a sugar plant syrup extract.

The nutriprotective amount of a sugar plant syrup extract may be from about 0.0020% to about 0.10% sugar plant syrup extract.

The nutriprotective amount of a sugar plant syrup extract may be from about 0.0027% to about 0.1023% sugar plant syrup extract.

The sugar plant syrup may be a sugar plant syrup derived products. The sugar plant syrup derived products may be butter, granulated sugar, hardened sugar, soft sugar, taffy, sugar plant syrup filtration residue, rejection of product generation, or combinations thereof.

The sugar plant extract may be concentrated sugar plant water issued from reverse osmosis, concentrated sugar plant water issued from pre-boiling nanofiltration, pasteurized sugar plant water, sterilized sugar plant water and extracts from sap, concentrated sap, a sugar plant syrup, a syrup filtration residue, samara, fruits, seeds, stem, leaves, twigs, roots, heartwood, sap wood, and bark, a rejection residue from the preparation of any one of the extracts, or combinations thereof.

The sugar plant may be chosen from maple tree, birch tree, sugar cane, sugar beet, corn, rice, palm tree, and agave.

The sugar plant syrup extract may be chosen from a methanol extract, a butanol extract, a butanol extract with sugar, a butanol extract without sugar, an ethyl acetate extract, an ethanol extract, a methyl tert-butyl ether extract a resin purified maple syrup extract (MSX), or combinations thereof.

The sugar plant syrup extract may have a hepatoprotective effect.

The butanol extract may have a hepatoprotective effect.

In a second embodiment, there is disclosed a method of eliciting a nutriprotective effect in a subject, which comprises administering a nutriprotective amount of a diet according to the present invention.

The nutriprotective effect may be a nutritherapy or a hepatoprotective effect.

The hepatoprotective effect may be a down-regulation in the cellular amino acid metabolism of the liver.

The hepatoprotective effect may be a down-regulation in the liver production of ammonia-forming enzymes.

The hepatoprotective effect may comprise a down-regulation in the subject serum level of aspartate aminotransferase (AST), alanine aminotransferase (ALT) and/or lactate dehydrogenase (LDH).

In a third embodiment, there is disclosed a method of treating a subject with a disorder, which comprises administering a nutritherapeutic amount of a diet according to the present invention.

The disorder may be liver disorder, inflammatory disease, cancer, diabetes, cardio-vascular disease, neurodegenerative disease, and a memory loss.

The liver disorder may be metabolic syndrome, damaged hepatic function, hepatic acid liver, dyslipidemia, hepatitis and liver cancer.

In another embodiment, there is disclosed a use of a nutriprotective diet according to the present invention for the preparation of a medicament for the treatment of a disorder in a subject.

In another embodiment, there is disclosed a use of a nutriprotective diet according to the present invention for the treatment of a disorder in a subject.

The disorder may be liver disorder, inflammatory disease, cancer, diabetes, cardio-vascular disease, neurodegenerative disease, and a memory loss.

The liver disorder may be metabolic syndrome, damaged hepatic function, hepatic acid liver, dyslipidemia, hepatitis and liver cancer.

In another embodiment, there is disclosed a nutriprotective carrier comprising a sugar plant syrup, a sugar plant syrup extract, a sugar plant extract, or combinations thereof for synergistic uptake and/or administration of at least one dietary supplement selected from the group consisting of pharmaceutical and neutraceutical compounds, functional food, and natural health products.

The carrier may be chosen from a drinking liquid, an energy drink, a therapeutic drink, and a protein rich drink.

The carrier may be a coating on a dietary supplement.

According to another embodiment, there is provided a method of preventing or treating a disorder in a patient; which comprises administering at least one dietary supplement selected from the group consisting of pharmaceutical and neutraceutical compounds, functional food, and natural health products in combination with the carrier of the present invention, wherein the carrier is administered concurrently or prior to the supplement.

According to an embodiment, there is provided a process for the extraction of polyphenolic compounds from maple syrup, which may comprise
  a) contacting an adsorbent material having a maple syrup polyphenolic fraction adsorbed thereon with an organic solvent, for a time sufficient and for a number of times sufficient, to elute and collect the maple syrup polyphenolic fraction.

The time sufficient may be about 30 minutes.

The number of times sufficient may be from about 1 time to about 3 times.

The process of the present in wherein prior to step a), a maple syrup mixture is adsorbed on said adsorbent material for a time sufficient to adsorb said polyphenolic fraction on said adsorbent material, wherein said mixture comprises maple syrup diluted in water.

The time sufficient to adsorb the polyphenolic fraction may be about 12 to about 20 hours.

The time sufficient to adsorb the polyphenolic fraction may be about 16 hours.

The process may be further comprising the step of diluting a maple syrup in water prior to adsorption on the adsorbent material.

The process may be further comprising the step of washing the adsorbent material with water prior to step a).

The process may be further comprising step b):
  2) heating the collected polyphenolic fraction to evaporate the organic solvent and obtain a dried polyphenolic fraction.

The heating is at a temperature of about 37° C. to about 40° C.

The organic solvent is chosen from methanol, ethyl acetate, butanol, ethanol, methyl tert-butyl ether, and combinations thereof.

The adsorbent material may be chosen from Amberlite™ XAD-4, Amberlite™ XAD-2, Amberlite™ XAD-7, Amberlite™ XAD 7HP, Amberlite™ XAD16, Amberlite™ XAD16HP, Amberlite™ XAD761, Amberlite™ XAD1180, Amberlite™ XAD1600, Amberlite™ XFS-4257, Amberlite™ XFS-4022, Amberlite™ XUS-40323, Amberlite™ XUS-40322, Amberlite™ FPX66, Amberlite™ strong anion exchange (SAX), Amberlite™ WAX, a pentafluorophenyl derivatived silica gel, HLB (hydrophobic-lipophilic balanced) type SILIaPrepX phase, a strong anion exchange (SAX) resin on silica, a mixed-mode strong anion exchange (SAX)-$C_{18}$, an aqueous $C_{18}$ phase, a $C_{18}$ phase, a $C_{18}$ type SILIaPrepX™ phase, diatomaceous earth.

The process may be further comprising prior to step a) an extraction with a mixture of solids for extraction of a sugar from the maple syrup.

The extraction with a mixture of solids comprises extraction with $MgSO_4$, NaCl, and a solid absorbent.

The solid absorbent may be chosen from an aminated silica resin, a $C_{18}$ silica resin, or combinations thereof.

The process may be further comprising prior to step a) a liquid-liquid extraction of said maple syrup.

The liquid-liquid extraction may comprise an ethyl acetate extraction, a butanol extraction, or combinations thereof, followed by adsorption on a silicon dioxide ($SiO_2$)/magnesium oxide (MgO) solid phase having a ratio of about 85% $SiO_2$ and about 15% MgO.

According to an embodiment, there is provided an extract obtained from the process of the present invention.

The following terms are defined below.

The term "sugar plant" is intended to mean maple tree, birch tree, sugar cane, sugar beet, corn, rice, palm tree, and agave.

The term "maple tree" is intended to mean a maple tree of a species known to date, such as *Acer nigrum, Acer lanum, Acer acuminatum, Acer albopurpurascens, Acer argutum, Acer barbinerve, Acer buergerianum, Acer caesium, Acer campbellii, Acer campestre, Acer capillipes, Acer cappadocicum, Acer carpinifolium, Acer caudatifolium, Acer caudatum, Acer cinnamomifolium, Acer circinaturn, Acer cissifolium, Acer crassum, Acer crataegifolium, Acer davidii, Acer decandrum, Acer diabolicum, Acer distylum, Acer divergens, Acer erianthum, Acer erythranthum, Acer fabri, Acer garrettii, Acer glabrum, Acer grandidentatum, Acer griseum, Acer heldreichii, Acer henryi, Acer hyrcanum, Acer ibericum, Acer japonicum, Acer kungshanense, Acer kweilinense, Acer laevigatum, Acer laurinum, Acer lobelii, Acer lucidum, Acer macrophyllum, Acer mandshuricum, Acer maximowiczianum, Acer miaoshanicum, Acer micranthum, Acer miyabei, Acer mono, Acer mono x Acer truncatum, Acer monspessulanum, Acer negundo, Acer ningpoense, Acer nipponicum, Acer oblongum, Acer obtusifolium, Acer oliverianum, Acer opalus, Acer palmatum, Acer paxii, Acer pectinatum, Acer pensylvanicum, Acer pentaphyllum, Acer*

*pentapomicum, Acer pictum, Acer pilosum, Acer platanoides, Acer poliophyllum, Acer pseudoplatanus, Acer pseudosieboldianum, Acer pubinerve, Acer pycnanthum, Acer rubrum, Acer rufinerve, Acer saccharinum, Acer saccharum, Acer sempervirens, Acer shirasawanum, Acer sieboldianum, Acer sinopurpurescens, Acer spicatum, Acer stachyophyllum, Acer sterculiaceum, Acer takesimense, Acer tataricum, Acer tegmentosum, Acer tenuifolium, Acer tetramerum, Acer trautvetteri, Acer triflorum, Acer truncatum, Acer tschonoskii, Acer turcomanicum, Acer ukurunduense, Acer velutinum, Acer wardii, Acer x peronai, Acer x pseudoheldreichii* or any new species not yet known.

The term "sugar plant syrup" is intended to mean sugar plant syrup and sugar plant syrup derived products, such as butter, sap butter, granulated sugar, hardened sugar, soft sugar, taffy, sugar plant syrup filtration residue, and any rejection of product generation.

The term "sugar plant extract" is intended to mean extracts from the sap, samara, fruits, seeds, stem, leaves, twigs, roots, heartwood, sap wood, bark, as well as concentrated sugar plant water issued from reverse osmosis, concentrated sugar plant water issued from pre-boiling nanofiltration, pasteurized sugar plant water, and sterilized sugar plant water.

The term "sugar plant syrup extract" is intended to mean methanol extract, a butanol extract, a butanol extract with sugar, a butanol extract without sugar, an ethyl acetate extract, an ethanol extract, a methyl tert-butyl ether extract, extract obtained from purification resin extractions, or combinations thereof.

The term "nutriprotective" is intended to mean nutriprotective and nutritherapy of any disorders or diseases in a subject including, without limitation, liver disorder, inflammatory disease, cancer, diabetes, cardio-vascular disease and neurodegenerative disease, wherein in the case of liver it is referred to as "hepatoprotective".

The term "dietary supplement" is also intended to mean sugar plant extracts or synthetic equivalents thereof, cosmeceutical, pharmaceutical, and neutraceutical compounds, functional food, and natural health products.

The term "hepatoprotective" is intended to mean any one of a diet, a compound, a composition, a method, a treatment with the ability to prevent damage to the liver.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

DETAILED DESCRIPTION OF THE PREFERRED EMBODIMENTS

A maple syrup product (medium grade), slightly brownish in color, is provided by the Federation of Maple Syrup Producers of Quebec (Quebec, Canada). It consists of 33% water, 61.0% sucrose, 0.5% glucose, 0.3% fructose, 1.8% saccharide (oligosaccharides and polysaccharides), 0.40% protein derived compounds, 0.25% minerals, 0.15% organic acid, 0.10% vitamins, 0.02% phenolic compounds, 0.002% amino acid, and 0.0001% phytohormones.

Three-week-old male Wistar rats, weighting about 51 g in average, are purchased from Charles River Japan (Kanagawa, Japan). They are quarantined and conditioned by administration of the AIN93G diet (Research Diets, New Brunswick, N.J., USA) for 4 days under the following conditions: temperature, 24±1° C.; relative humidity, 48±4%; and artificial lighting, 12 hours/day (8:00-20:00).

Figure 1:
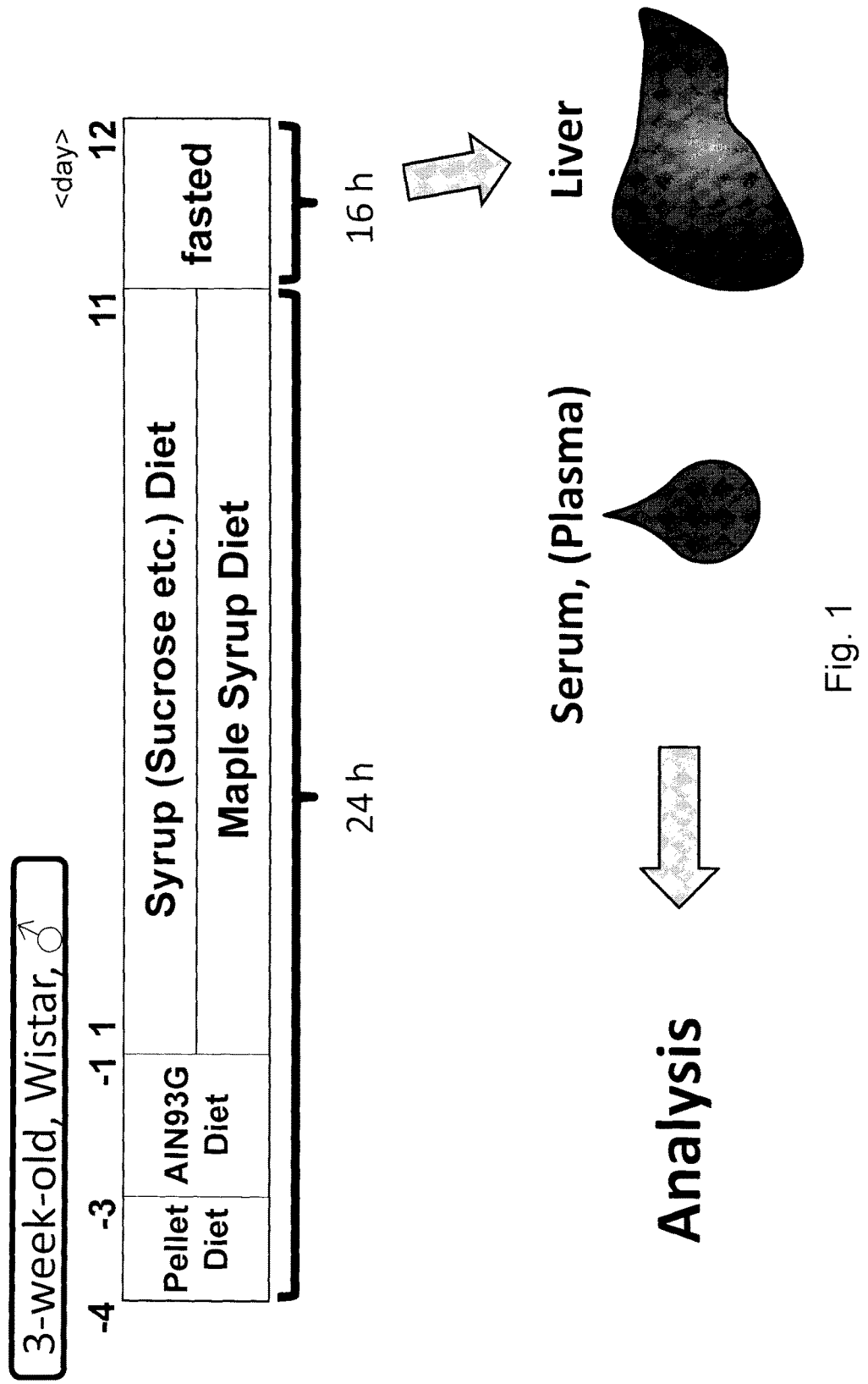
FIG. 1 illustrates the diet schedule and biological sample analysis procedure for the tested subjects.

Rats had free access to the diet and drinking water during this acclimatizing period. For feeding tests, they are dichotomized (n=7 and 8) for maple syrup and sugar mix syrup group, respectively, and then fed for 11 days on either the AIN93G diet containing 20% maple syrup or on the 20% sugar mix syrup with a similar sugar composition (FIG. 1). The amount of maple syrup or the sugar mix syrup is arranged by taking into consideration the amounts of sucrose and β-corn starch added in each diet. Subsequently, rats in both diet groups are fasted for 16 hours, prior to being anesthetically sacrificed for dissection. Immediately after, blood sample is taken from carotid artery of each rat for the following biochemical investigations by Nagahama Life Science Laboratory (Shiga, Japan).

Figure 2:
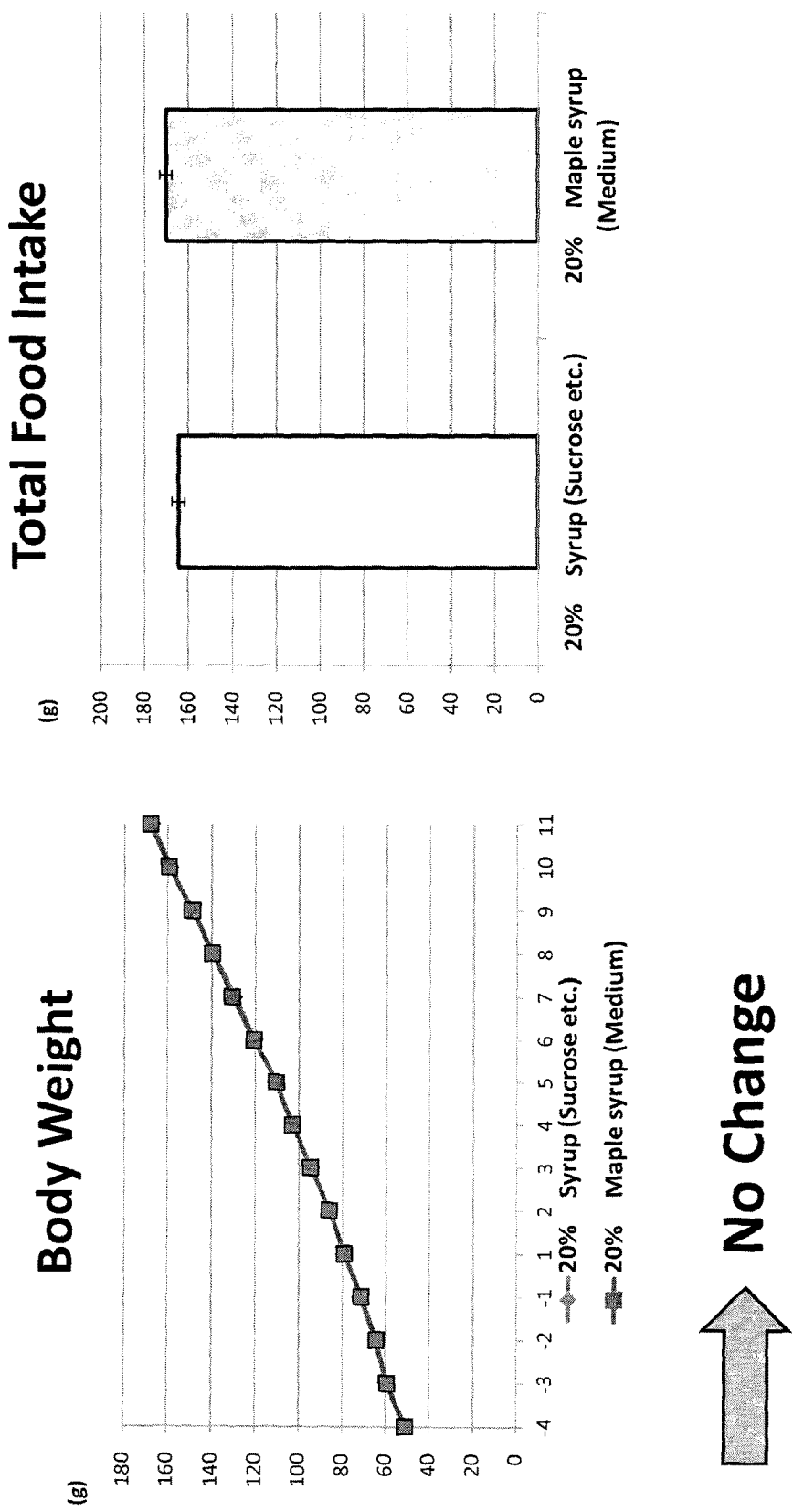
FIG. 2 illustrates the body weight and total food intake of the tested subjects.
Figure 3:
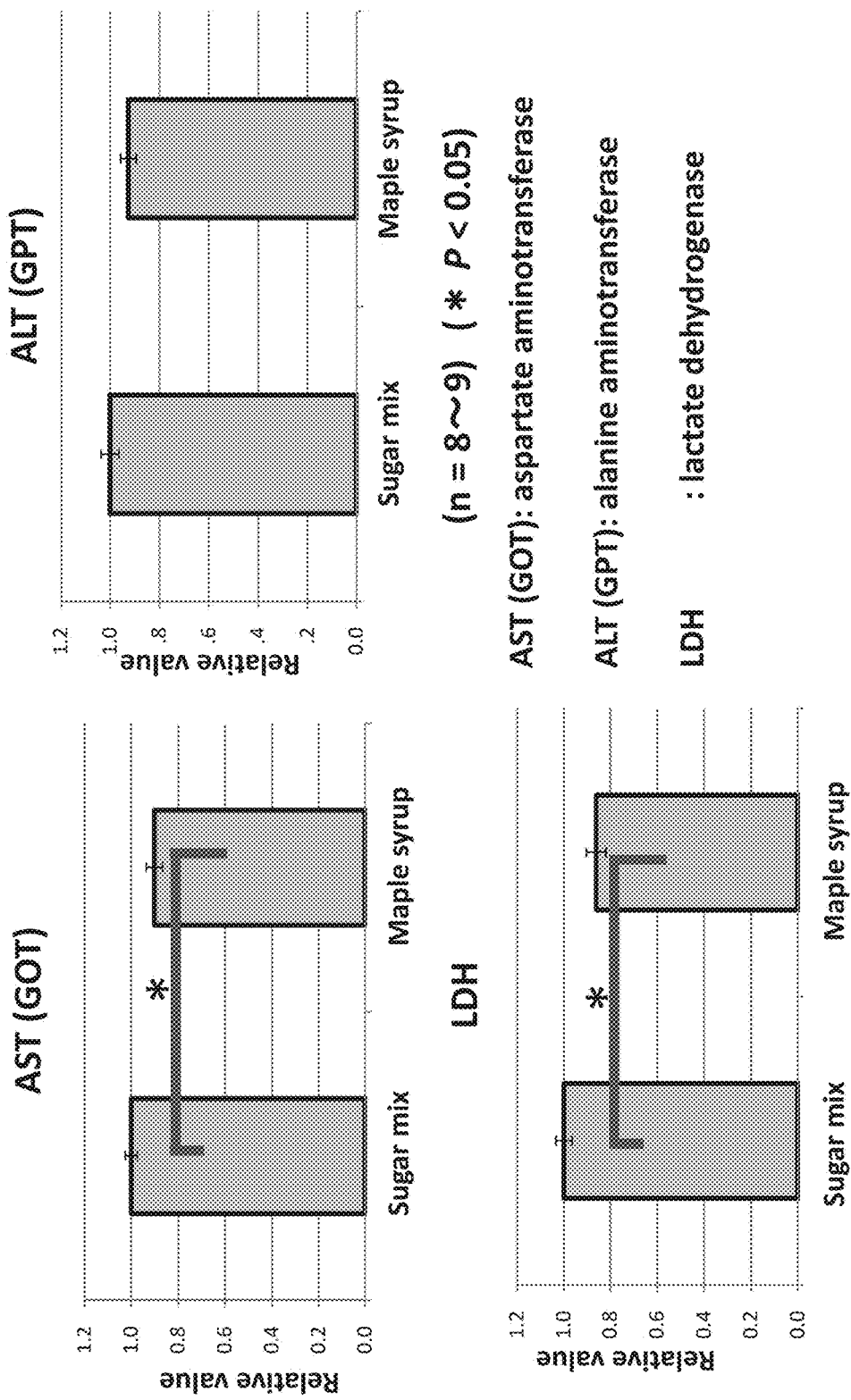
FIG. 3 illustrates the subjects' blood biochemistry.
Figure 4:
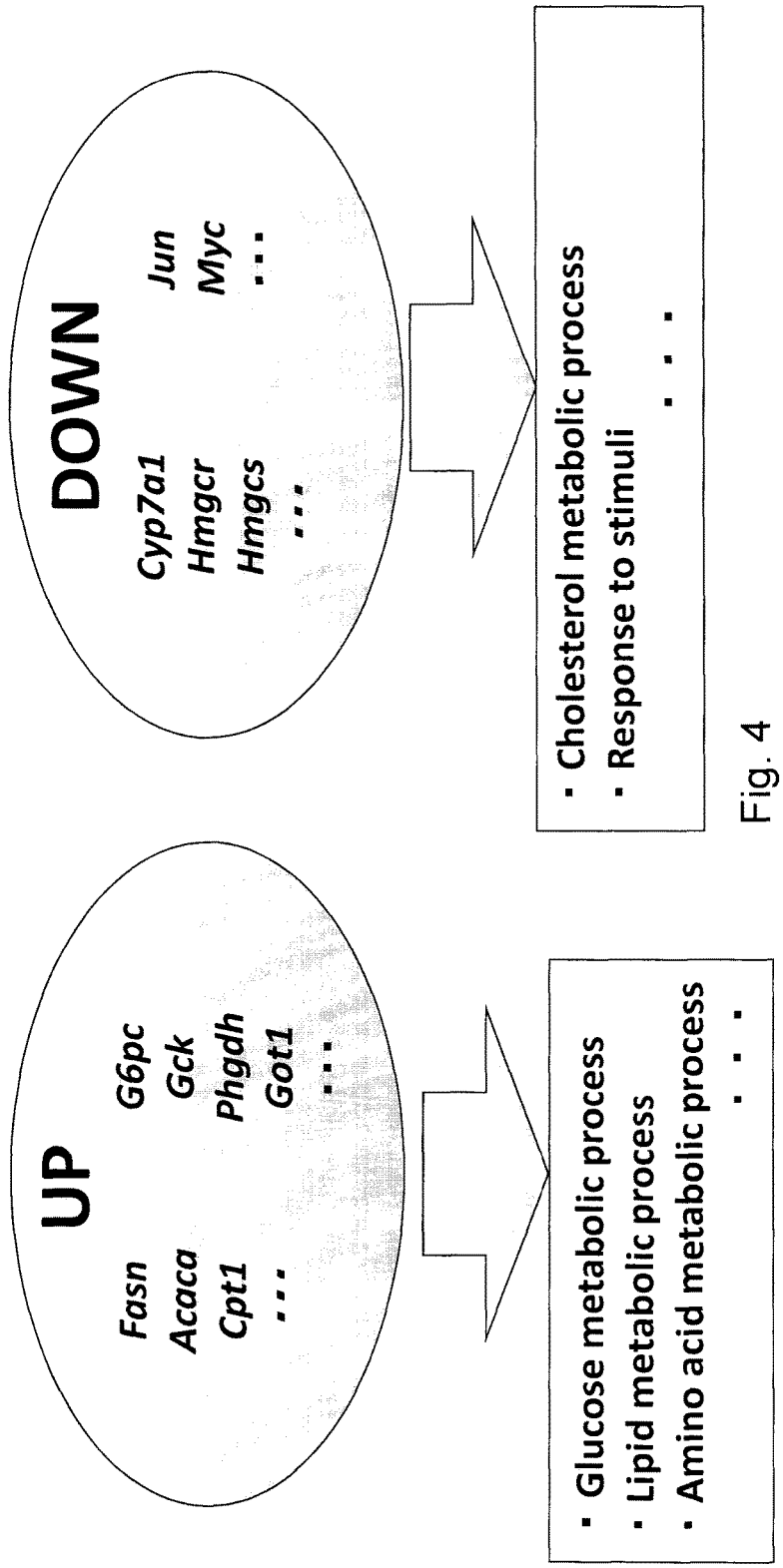
FIG. 4 illustrates the methods of DNA microarray data analysis.

No significant diet difference is observed either in the total food intake or in the time-course body weight gain (FIG. 2). It should be noted that rats preferred maple syrup as well as the simulated sugar mix syrup without any sensory rejection. The serum biochemical parameters of the rats fed the maple syrup-containing diet, when compared to those fed the control, did not show significant differences in the levels of serum glucose, total cholesterol and triglyceride. While these metabolic parameters are similar to each other, there are important differences in the serum levels of aspartate aminotransferase (AST) alanine aminotransferase (ALT) and lactate dehydrogenase (LDH), as liver impairment markers (FIG. 3). In particular, there are significant decreases in AST and LDH (P<0.05) (Table 1).

TABLE 1

Serum Biochemical Parameters† Investigated

|  | Sugar mix syrup | Maple syrup |
|---|---|---|
| AST, IU/L | 219.4 ± 9.5 | 185.6 ± 10.1* |
| ALT, IU/L | 35.5 ± 2.3 | 31.9 ± 1.6 |
| LDH, IU/L | 3079.5 ± 173.8 | 2478.0 ± 179.1* |
| Glucose, mg/dL | 51.0 ± 7.1 | 51.7 ± 4.5 |
| Total cholesterol, mg/dL | 73.0 ± 3.4 | 80.2 ± 5.1 |
| Triglyceride, mg/dL | 66.1 ± 15.5 | 56.1 ± 9.8 |

Values are represented as the means ± SEM for n = 8 and n = 7 in the sugar mix syrup and the maple syrup, respectively.
†AST, aspartate aminotransferase; ALT, alanine aminotransferase; LDH, lactate dehydrogenase.
*P < 0.05, for between-diet differences A total RNA sample is prepared from the liver and 6 randomized samples are subjected to microarray analysis using GeneChip Rat Genome 230 2.0 Array (Affymetrix, Santa Clara, Calif., USA). The obtained microarray data (CEL files) are quantified with the distribution free weighted method (DFW) using the statistical language Rand Bioconductor.

All the microarray data are submitted to the National Center for Biotechnology Information (NCBI) Gene Expression Omnibus (GEO Series ID GSE30532). To determine specific effects of maple syrup on gene expression, differentially expressed genes (DEGs) between the two groups are identified by applying the rank products (RP) method to the DFW quantified data.

Figure 5:
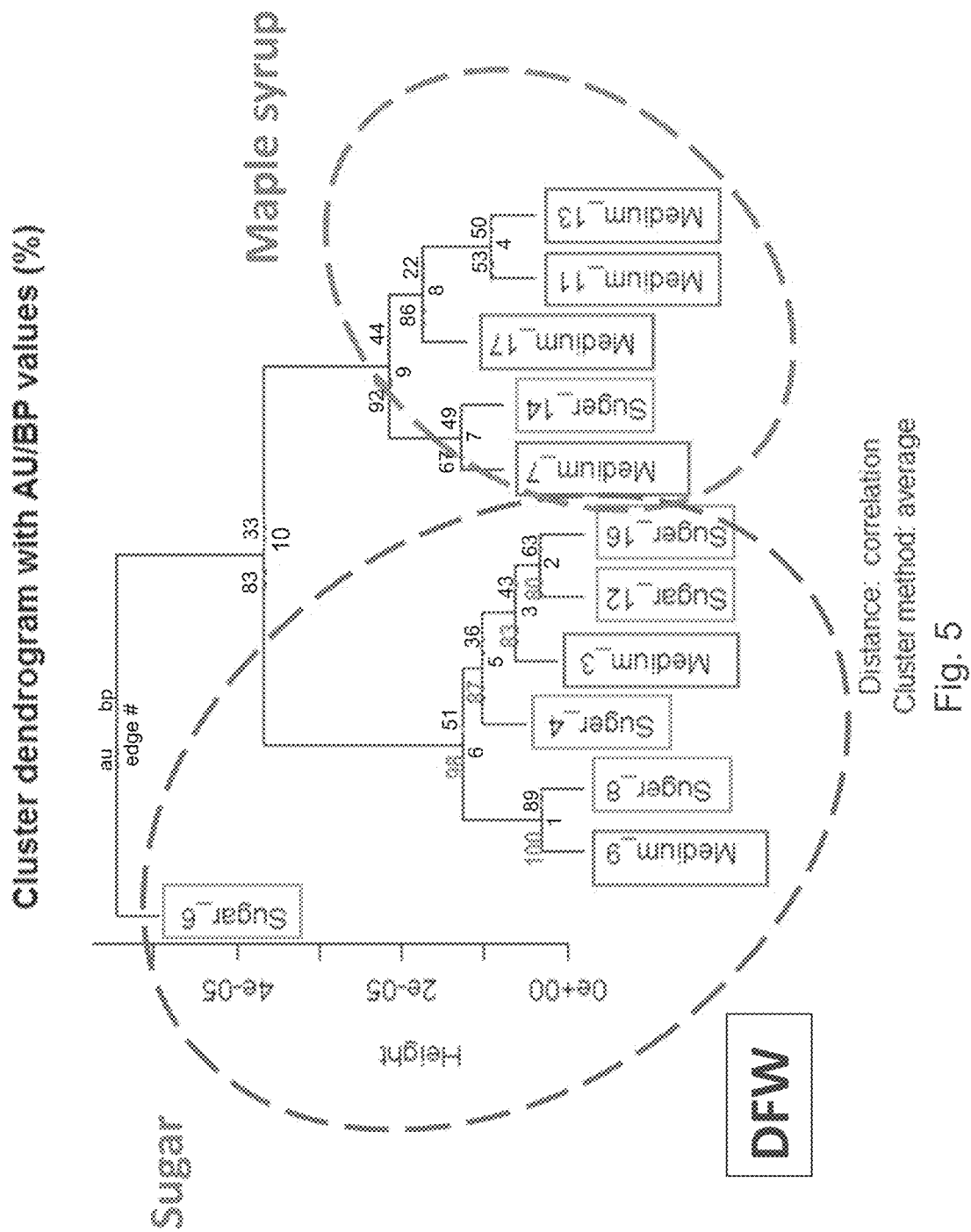
FIG. 5 illustrates hierarchical clustering.

Using the false discovery rate (FDR) significance <0.05, 246 up-regulated and 236 down-regulated genes is selected. To identify over-represented Gene Ontology (GO) terms in the DEGs, a functional annotation tool in the Database for Annotation, Visualization, and Integrated Discovery (DAVID) and QuickGO are used. GO terms with Benjamini and Hochberg FDR-corrected P-value less than 0.05 are regarded as significantly enriched. Such GO terms for genes that are up- or down-regulated by maple syrup intake are summarized in Table 2 and FIGS. 5 and 6.

TABLE 2

Significantly Enriched GO Term (FDR-corrected P-value 0 05) Identified among the Top 246 Up-(A) and 236 Downregulated (B) Genes

| GO_ID | Term | FDR-corrected P-value |
|---|---|---|
| | A | |
| 0050896 | response to stimulus | 2.63E-02 |
| 0065007 | biological regulation | |
| 0065008 |   regulation of biological quality | |
| 0010817 |     regulation of hormone levels | 1.54E-01 |
| 0042445 |     hormone metabolic process | 2.97E-02 |
| 0008152 | metabolic process | 3.18E-01 |
| 0055114 |   oxoacid reduction process | |
| 0044237 |   cellular metabolic process | |
| 0006082 |     organic acid metabolic process | 3.02E-02 |
| 0043436 |       oxoacid metabolic process | 3.70E-02 |
| 0019752 |       carboxylic acid metabolic process | 3.70E-02 |
| 0042180 |     cellular ketone metabolic process | 2.91E-02 |
| 0044281 |   small molecule metabolic process | |
| 0002376 | immune system process | |
| 0019882 |   antigen processing and presentation | 2.33E-01 |
| 0048002 |     antigen processing and presentation of peptide antigen | 1.23E-01 |
| 0002474 |       antigen processing and presentation of peptide antigen via MHC class I | 4.48E-02 |

TABLE 2-continued

Significantly Enriched GO Term (FDR-corrected P-value 0 05) Identified among the Top 246 Up-(A) and 236 Downregulated (B) Genes

| GO_ID | Term | FDR-corrected P-value |
|---|---|---|
| B | | |
| 0050896 | response to stimulus | 7.59E-02 |
| 0042221 | response to chemical stimulus | 3.65E-02 |
| 0002376 | immune system process | |
| 0019882 | antigen processing and presentation | 1.55E-02 |
| 0019740 | nitrogen utilization | |
| 0009308 | amine metabolic process | 7.75E-02 |
| 0009310 | amine catabolic process | 3.20E-02 |
| 0009987 | cellular process | |
| 0044106 | cellular amine metabolic process | 3.67E-02 |
| 0006520 | cellular amino acid metabolic process | 3.83E-02 |
| 0019752 | carboxylic acid metabolic process | 7.21E-03 |
| 0043436 | oxoacid metabolic process | 7.21E-03 |
| 0042180 | cellular ketone metabolic process | 3.29E-03 |
| 0006082 | organic acid metabolic process | 3.97E-03 |
| 0044237 | cellular metabolic process | 8.52E-01 |
| 0044248 | cellular catabolic process | 3.96E-02 |
| 0009056 | catabolic process | 6.51E-02 |
| 0008152 | metabolic process | 6.81E-01 |

GO terms with no P-value indicate no significance.
FDR-corrected P-value of the categories appearing the deepest hierarchy are shadowed The up-regulated GO terms included antigen processing-presentation, carboxylic acid (including amino acid) metabolism, oxidoreduction, hormone metabolism, and response to external stimulus (Table 2A), as well as negative regulation of transcription, glutamine family amino acid metabolic process, response to organic substance, response to drug, whereas the down-regulated GO terms comprised amine catabolism, cellular amino acid metabolism, aspartate family acid metabolic process, antigen processing-presentation and response to chemical stimulus (Table 2B).

Figure 6:
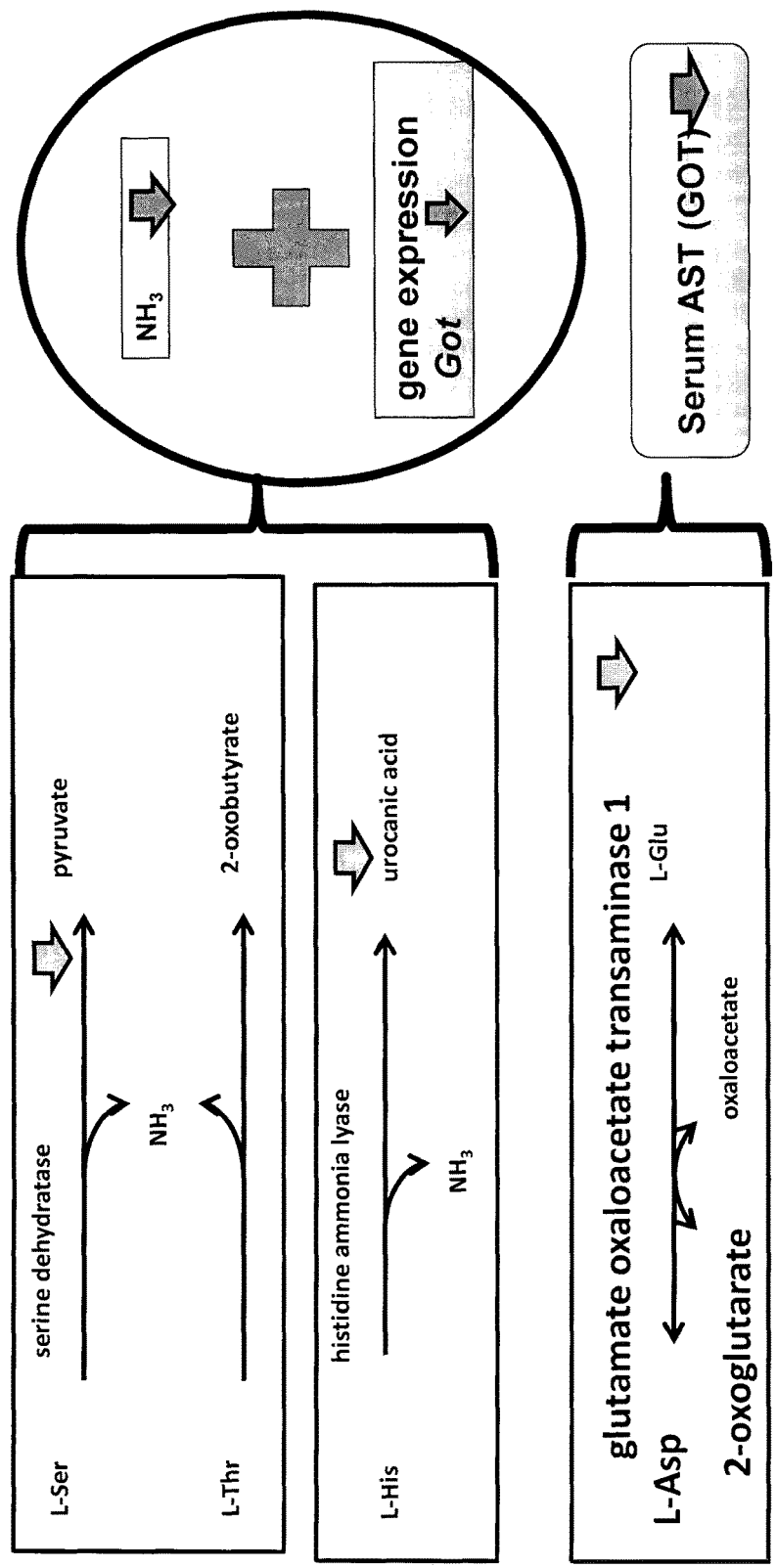
FIG. 6 illustrates the down-regulated genes for amino acid metabolysing enzymes.
Figure 7:
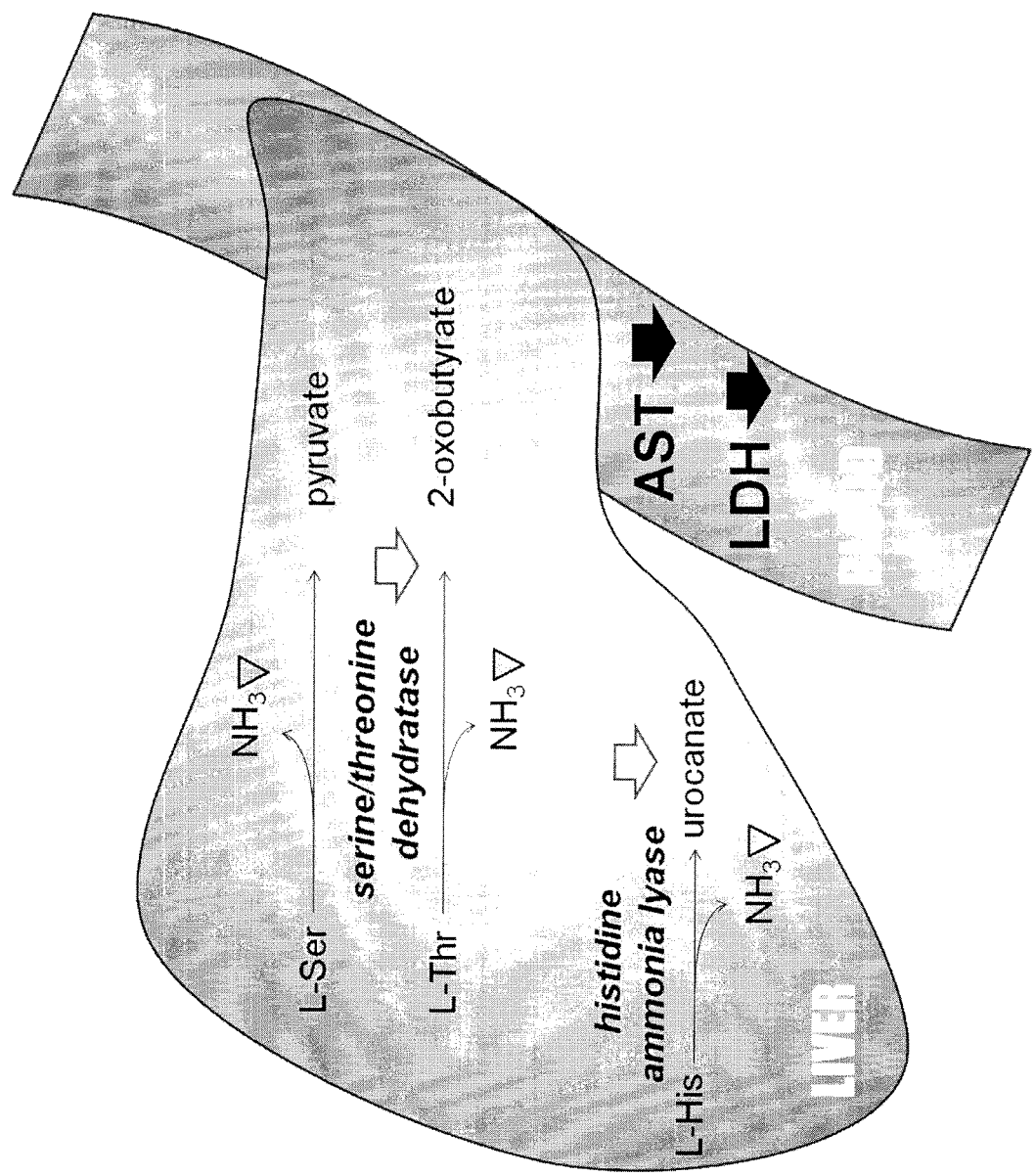
FIG. 7 illustrates the down-regulation of the cellular amino acid metabolic process of ammonia-forming enzymes such as serine/threonine dehydratase and histidine ammonia-lyase.

It is noted that genes for cellular amino acid metabolic process is down-regulated, including those for ammonia-forming enzymes such as serine/threonine dehydratase and histidine ammonia-lyase (FIGS. 6-7). In general, the excessive formation of free ammonia in the body is harmful to the liver, resulting in increased values of AST, ALT and LDH.

Some cases have been reported where administration of 20% casein diet activates serine/threonine dehydratase. Threonine is known as an amino acid that is difficult to metabolize and that can be better metabolized when it is ingested together with casein, leading to induction of threonine dehydratase activity for production of 2-oxobutyrate and ammonia. The high content of casein (20%) in AIN93G diet may probably enhance the activity of serine/threonine dehydratase to liberate ammonia (FIGS. 6-7).

It is likely that the enhancement can be countered when the gene for this enzyme is down-regulated by administration of maple syrup. On the other hand, mRNA level of the gene for AST is down-regulated. This should also participate in down-regulation of serum AST. The present document is the first to describe a piece of body-protecting effects of ingested maple syrup.

In embodiments there are disclosed phenolic extracts and compounds from Canadian maple syrup (MS) and from maple trees (e.g. red, silver, or sugar maple). The compounds and extracts may be used for their hepatoprotective properties.

In other embodiments there are disclosed twenty-three phenolic compounds isolated from a butanol extract of Canadian maple syrup (MS) using chromatographic methods. The compounds are identified from their nuclear magnetic resonance and mass spectral data as seven lignans:

lyoniresinol (1), secoisolariciresinol (2), dehydroconiferyl alcohol (3), 5'-methoxy-dehydroconiferyl alcohol (4), erythro-guaiacylglycerol-β-O-4'-coniferyl alcohol (5), erythro-guaiacylglycerol-β-O-4'-dihydroconiferyl alcohol (6), and [3-[4-[(6-deoxy-α-L-mannopyranosyl)oxy]-3-methoxyphenyl]methyl]-5-(3,4-dimethoxyphenyl)dihydro-3-hydroxy-4-(hydroxymethyl)-2(3H)-furanone (7);

two coumarins: scopoletin (8) and fraxetin (9);

a stilbene: (E)-3,3'-dimethoxy-4,4'-dihydroxystilbene (10), and thirteen phenolic derivatives: 2-hydroxy-3',4'-dihydroxyacetophenone (11), 1-(2,3,4-trihydroxy-5-methylphenyl)-ethanone (12), 2,4,5-trihydroxyacetophenone (13), catechaldehyde (14), vanillin (15), syringaldehyde (16), gallic acid (17), trimethyl gallic acid methyl ester (18), syringic acid (19), syringenin (20), (E)-coniferol (21), C-veratroylglycol (22), and catechol (23).

The antioxidant activities of the MS extract, pure compounds, vitamin C ($IC_{50}$=58 μM), and the synthetic commercial antioxidant, butylatedhydroxytoluene ($IC_{50}$=2651 μM), are evaluated in the diphenylpicrylhydrazyl (DPPH) radical scavenging assay. Among the isolates, the phenolic derivatives and coumarins showed superior antioxidant activity ($IC_{50}$<100 μM) compared to the lignans and stilbene ($IC_{50}$>100 μM).

General Experimental Procedures $^1$H and $^{13}$C Nuclear Magnetic Resonance (NMR) spectra are obtained either on a Bruker™ 400 MHz or a Varian™ 500 MHz instrument using deuterated methanol (CD3OD) as solvent. Electrospray ionization mass spectral (ESIMS) data are acquired on a Q-Star Elite (Applied Biosystems MDS) mass spectrometer equipped with a Turbo Ionspray source and are obtained by direct infusion of pure compounds. Analytical high performance liquid chromatography (HPLC) are performed on a Hitachi Elite LaChrom™ system consisting of a L2130 pump, L-2200 autosampler, and a L-2455 Diode Array Detector all operated by EZChrom™ Elite software. Semi-preparative scale HPLC are performed on a Beckman-Coulter HPLC system consisting of a Beckman System Gold™ 126 solvent module pump, 168 photodiode array (PDA)-UV/VIS detector, and 508 autosampler all operated by the 32 Karat 8.0 software. All solvents are either ACS or HPLC grade and are obtained from Wilkem Scientific (Pawcatuck, R.I.). Ascorbic acid (vitamin C), butylatedhydroxytoluene (BHT), and diphenylpicrylhydrazyl (DPPH) reagent are purchased from Sigma-Aldrich (St Louis, Mo.).

Maple Syrup (MS) Butanol Extract

Maple syrup (grade C, 20 L) is provided by the Federation of Maple Syrup Producers of Quebec (Canada). The syrup is kept frozen until extraction when it is subjected to liquid-liquid partitioning with ethyl acetate (10 L×3) followed by n-butanol (10 L×3) solvents, to yield ethyl acetate (4.7 g) and butanol (108 g) extracts, respectively, after solvent removal in vacuo.

Analytical HPLC

All analyses are conducted on a Luna C18 column (250× 4.6 mm i.d., 5 µM; Phenomenex) with a flow rate at 0.75 mL/min and injection volume of 20 µL. A gradient solvent system consisting of solvent A (0.1% aqueous trifluoroacetic acid) and solvent B (methanol, MeOH) is used as follows: 0-10 min, 10% to 15% B; 10-20 min, 15% B; 20-40 min, 15% to 30% B; 40-55 min, 30% to 35% B; 55-65 min, 35% B; 65-85 min, 35% to 60% B; 85-90 min, 60% to 100% B, 90-93 min, 100% B; 93-94 min, 100% to 10% B; 94-104 min, 10% B. FIGS. 1A and 1B show the HPLC-UV profiles of the butanol extract and all of the isolated phenolics (combined into one solution/injection), respectively.

Isolation of Compounds from the MS Butanol Extract

The butanol extract (108 g) is extracted with methanol (100 mL×3) to afford methanol soluble (57 g; dark-brown powder) and methanol insoluble (51 g; off-white powder) fractions. Analytical HPLC analyses of the methanol soluble extract revealed a number of peaks characteristic of phenolic compounds at 220, 280 and 360 nm (see above for details of methodology; see FIG. 1A for chromatogram). Therefore, this fraction is selected for further purification by repeated chromatography on a Sephadex™ LH-20 column (4.5×64 cm), eluting with a gradient system of MeOH: $H_2O$ (3:7 v/v to 7:3 v/v to 100:0 v/v), and then with acetone: $H_2O$ (7:3 v/v). Based on analytical HPLC profiles, twelve combined fractions, Fr. 1-12, are obtained. Fr. 4 (1.5 g) is subjected to column chromatography on a Sephadex™ LH-20 column (4.5×64 cm) using a gradient solvent system of MeOH: $H_2O$ (3:7 v/v to 7:3 v/v) to afford twelve sub-fractions, Fr. 4.1-4.12. These are individually subjected to a series of semi-prep HPLC separation using a Waters Sunfire Prep™ $C_{18}$ column (250×10 mm i.d., 5 µm; flow 2 mL/min) and eluting with a MeOH:$H_2O$ gradient system to yield compounds 1 (4.6 mg), 3 (3.8 mg), 5 (4.0 mg), 6 (41.6 mg), 7 (6.6 mg), 11 (3.5 mg), 15 (0.3 mg), 16 (0.8 mg), 18 (0.2 mg), 20 (1.3 mg), 22 (1.5 mg) and 23 (3.0 mg). Similarly, Fr. 5 (0.47 g) is purified by semi-prep HPLC using a Waters XBridge Prep $C_{18}$ column (250×19 mm i.d., 5 µm; flow 3.5 mL/min) and a gradient solvent system of MeOH:$H_2O$ to afford four subfractions Fr. 5.1-5.4. These subfractions are separately subjected to a combination of semi-prep HPLC and/or Sephadex™ LH-20 column chromatography with gradient solvents systems of MeOH:$H_2O$ to afford compounds 2 (1.9 mg), 4 (1.9 mg), 8 (2.0 mg), 9 (2.3 mg), 14 (2.5 mg), 17 (2.4 mg), 19 (1.8 mg) and 21 (1.3 mg). Similarly, Fr. 6 (0.2 g) afforded compounds 12 (1.4 mg) and 13 (1.3 mg) and Fr. 11 yielded compound 10 (4.8 mg).

Isolation of Compounds from the MS Ethyl Acetate Extract

Maple syrup (grade C, 20 L) is provided by the Federation of Maple Syrup Producers of Quebec (Canada). The syrup (20 L) is kept in the freezer (−20° C.), until extraction when it is subjected to liquid-liquid partitioning with ethyl acetate (10 L×3) followed by n-butanol (10 L×3) solvents, to yield ethyl acetate (4.7 g) and butanol (108 g) extracts, respectively, after solvent removal in vacuo. The ethyl acetate extract (4.7 g) is subjected to a series of chromatographic isolation procedures using XAD-16, silica gel, Sephadex™-LH 20, and C-18 column chromatography. Semi-purified fractions obtained from these columns are then further subjected to prep-HPLC to yield twenty pure compounds.

Identification of Compounds

All of the isolated compounds are identified by examination of their $^1H$ and/or $^{13}C$ NMR and mass spectral data, and by comparison of these to published literature reports, when available (Table 3). The NMR data for compounds 7, 12, and 13 are provided here.

TABLE 3

Compounds identified in a butanol extract of Canadian maple syrup (MS)

| Identification | Structure |
| --- | --- |
| 1  lyoniresinol | 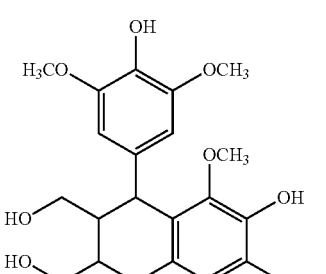 |

TABLE 3-continued

Compounds identified in a butanol extract of Canadian maple syrup (MS)

| Identification | Structure |
|---|---|
| 2 Secoisolariciresinol | 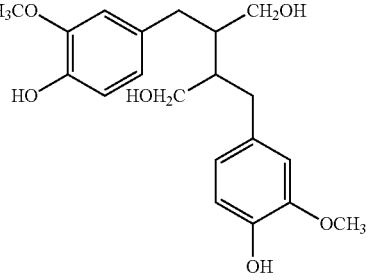 |
| 3 dehydroconiferyl alcohol | 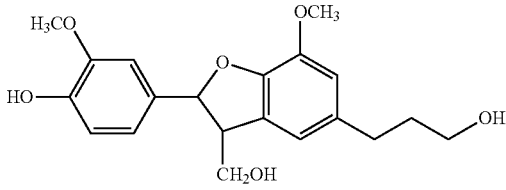 [SMILES: COc1cc(C2Oc3c(OC)cc(CCCO)cc3C2CO)ccc1O] |
| 4 5'-methoxydehydroconiferyl alcohol | 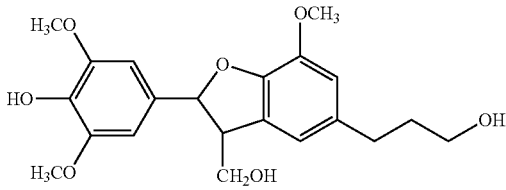 [SMILES: COc1cc(C2Oc3c(OC)cc(CCCO)cc3C2CO)cc(OC)c1O] |
| 5 guaiacylglycerol-β-O-4'-coniferyl alcohol (1,3-Propanediol, 1-(4-hydroxy-3-methoxyphenyl)-2-[4-[(1E)-3-hydroxy-1-propenyl]-2-methoxyphenoxy]-, (1R,2R)-) | 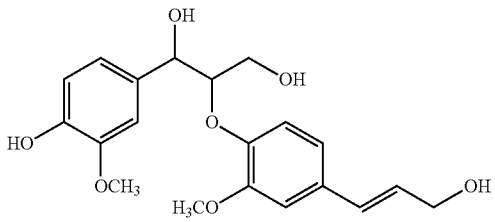 [SMILES: COc1cc(C(O)C(CO)Oc2ccc(/C=C/CO)cc2OC)ccc1O] |
| 6 guaiacylglycerol-β-O-4'-dihydroconiferyl alcohol 1-(4-hydroxy-3-methoxyphenyl)-2-[4-(3-hydroxypropyl)-2-methoxyphenoxy]-propane-1,3-diol | 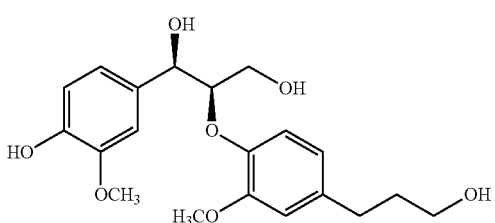 |
| 7 [3-[4-[(6-deoxy-α-L-mannopyranosyl)oxy]-3-methoxyphenyl]methyl]-5-(3,4-dimethoxyphenyl)dihydro-3-hydroxy-4-(hydroxymethyl)-2(3H)-furanone | 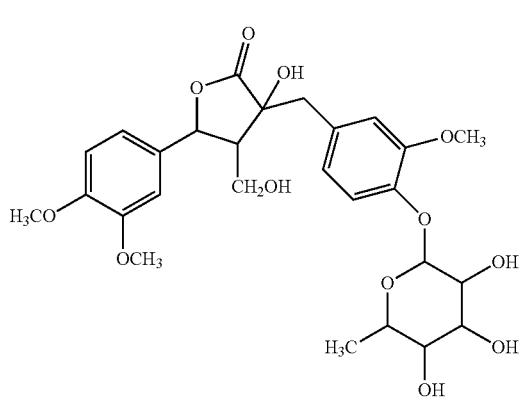 [SMILES: COc1ccc(C2OC(=O)C(O)(Cc3ccc(OC4OC(C)C(O)C(O)C4O)c(OC)c3)C2CO)cc1OC] |

TABLE 3-continued

Compounds identified in a butanol extract of Canadian maple syrup (MS)

| | Identification | Structure |
|---|---|---|
| 8 | Scopoletin | 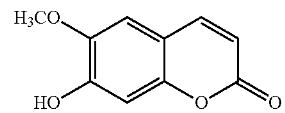 [SMILES: COc1cc2ccc(=O)oc2cc1O] |
| 9 | Fraxetin | 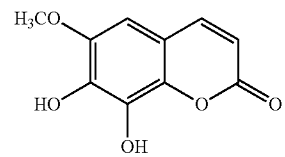 [SMILES: COc1cc2ccc(=O)oc2c(O)c1O] |
| 10 | (E)-3,3'-dimethoxy-4,4'-dihydroxystilbene | 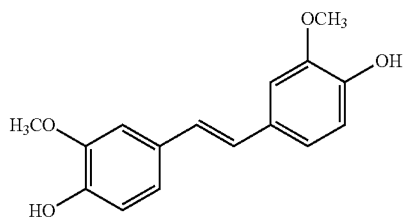 [SMILES: COc1cc(/C=C/c2ccc(O)c(OC)c2)ccc1O] |
| 11 | 2-hydroxy-3',4'-dihydroxyacetophenone | 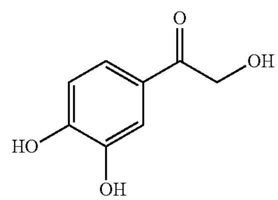 [SMILES: O=C(CO)c1ccc(O)c(O)c1] |
| 12 | 1-(2,3,4-trihydroxy-5-methylphenyl)-ethanone | 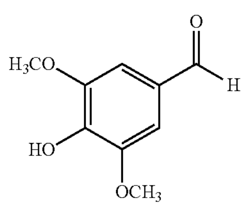 [SMILES: COc1cc(C=O)cc(OC)c1O] |
| 13 | 2,4,5-trihydroxyacetophenone | 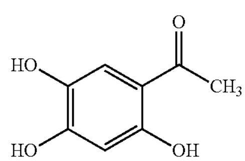 |
| 14 | Catechaldehyde | 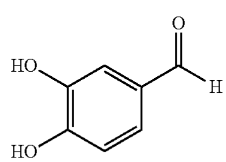 |
| 15 | Vanillin | 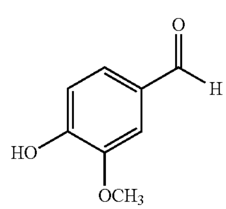 [SMILES: COc1cc(C=O)ccc1O] |

TABLE 3-continued

Compounds identified in a butanol extract of Canadian maple syrup (MS)

| Identification | Structure |
| --- | --- |
| 16 Syringaldehyde | |
| 17 gallic acid | |
| 18 trimethyl gallic acid methyl ester | |
| 19 syringic acid | |
| 20 Syringenin | |
| 21 (E)-coniferol | |
| 22 C-veratroylglycol | |
| 23 Catechol | |

TABLE 3-continued

Compounds identified in a butanol extract of Canadian maple syrup (MS)

| Identification | Structure |
|---|---|
| 54 Quebecol | (structure) |

In another embodiment, there are disclosed thirty phenolics obtained from an ethyl acetate extract of maple syrup (MS-EtOAc).

Chemicals and Reagents.

All solvents are of ACS or HPLC grade and are obtained from Sigma-Aldrich through Wilkem Scientific (Pawcatuck, R.I.). Sephadex LH-20, ascorbic acid, butylated hydroxytoluene (BHT), and diphenylpicrylhydrazyl (DPPH) reagent are purchased from Sigma-Aldrich (St. Louis, Mo.).

Extraction and Isolation of Maple Syrup Ethyl Acetate (MS-EtOAc) Compounds.

Maple syrup (grade C, 20 L) is provided by the Federation of Maple Syrup Producers of Quebec (Canada). The maple syrup is shipped and kept frozen upon delivery. The maple syrup is subjected to liquid-liquid partitioning with ethyl acetate (10 L×3) to yield a dried ethyl acetate extract (MS-EtOAc; 4.7 g) after solvent removal in vacuo. The MS-EtOAc (4.5 g) is initially purified on a Sephadex LH-20 column (4×65 cm) with a gradient system of MeOH/$H_2O$ (3:7 to 1:0, v/v) to afford seven fractions, A1-A7. Fraction A1 (2.08 g) is then chromatographed on a C18 MPLC column (4×37 cm) eluting with a gradient system of MeOH/$H_2O$ (3:7 to 1:0, v/v) to afford sixteen subfractions, B1-B16. These sub-fractions are individually subjected to a series of semi-preparative HPLC separations using a Phenomenex Luna C18 column (250×10 mm i.d., 5 μm, flow=2 mL/min) with different isocratic elution systems of MeOH/$H_2O$ to afford compounds 25 (0.9 mg), 26 (2.5 mg), 27 (0.8 mg), 28 (0.5 mg), 29 (17.5 mg), 730 (0.7 mg), 31 (1.1 mg), 32 (3.9 mg), 33 (1.1 mg), 34 (2.1 mg), 35 (2.8 mg), 36 (3.2 mg), 38 (2.4 mg), 39 (5.2 mg), 40 (0.8 mg), and 53 (0.5 mg). Similarly, fraction A3 (0.71 g) is purified by semi-preparative HPLC using a Waters XBridge Prep C18 column (250×19 mm i.d., 5 μm; flow=3.5 mL/min) and a gradient solvent system of MeOH/$H_2O$ to afford four subfractions C1-C4. These subfractions are separately subjected to semi-preparative HPLC with isocratic solvents systems of MeOH/$H_2O$ to afford compounds 24 (2.2 mg), 37 (4.5 mg), 42 (4.5 mg), 43 (2.2 mg), 44 (4.2 mg), 50 (3.7 mg), and 51 (1.1 mg). Similarly, fraction A4 (0.097 g) is purified by semi-preparative HPLC to afford compounds 41 (1.4 mg), 45 (2.6 mg), 46 (8.0 mg), 47 (0.4 mg), and 49 (3.2 mg) and subfraction A5 (0.022 g) yielded compounds 48 (3.6 mg) and 52 (1.1 mg).

TABLE 4

Total Compounds isolated from an Ethyl Acetate Extract of Canadian Maple Syrup (MS-EtOAc)

| compd | Identification |
|---|---|
| 1 | Lyoniresinol |
| 2 | Secoisolariciresinol |
| 6 | 1-(4-hydroxy-3-methoxyphenyl)-2-[4-(3-hydroxypropyl)-2-methoxyphenoxy]-propane-1,3-diol (guaiacylglycerol-β-O-4'-dihydroconiferyl alcohol) |
| 8 | Scopoletin |
| 22 | C-veratroylglycol |
| 24 | 5-(3",4"-dimethoxyphenyl)-3-hydroxy-3-(4'-hydroxy-3'-methoxybenzyl)-4-hydroxymethyl-dihydrofuran-2-one* |
| 25 | (erythro, erythro)-1-[4-[2-hydroxy-2-(4-hydroxy-3-methoxyphenyl)-1-(hydroxymethyl)ethoxy]-3,5-dimethoxyphenyl]-1,2,3-propanetriol* |
| 26 | (erythro, threo)-1-[4-[2-hydroxy-2-(4-hydroxy-3-methoxyphenyl)-1-(hydroxymethyl)ethoxy]-3,5-dimethoxyphenyl]-1,2,3-propanetriol* |
| 27 | (threo, erythro)-1-[4-[(2-hydroxy-2-(4-hydroxy-3-methoxyphenyl)-1-(hydroxymethyl)ethoxy]-3-methoxyphenyl]-1,2,3-propanetriol$^a$ |
| 28 | (threo, threo)-1-[4-[(2-hydroxy-2-(4-hydroxy-3-methoxyphenyl)-1-(hydroxymethyl)ethoxy]-3-methoxyphenyl]-1,2,3-propanetriol$^a$ |
| 29 | threo-guaiacylglycerol-β-O-4'-dihydroconiferyl alcohol |

TABLE 4-continued

Total Compounds isolated from an Ethyl Acetate Extract of Canadian Maple Syrup (MS-EtOAc)

| compd | Identification |
|---|---|
| 30 | erythro-1-(4-hydroxy-3-methoxyphenyl)-2-[4-(3-hydroxypropyl)-2,6-dimethoxyphenoxy]-1,3-propanediol[a] |
| 31 | 2-[4-[2,3-dihydro-3-(hydroxymethyl)-5-(3-hydroxypropyl)-7-methoxy-2-benzofuranyl]-2,6-dimethoxyphenoxy]-1-(4-hydroxy-3-methoxyphenyl)-1,3-propanediol |
| 32 | Acernikol |
| 33 | leptolepisol D[a] |
| 34 | buddlenol E[a] |
| 35 | (1S,2R)-2-[2,6-dimethoxy-4-[(1S,3aR,4S,6aR)-tetrahydro-4-(4-hydroxy-3,5-dimethoxyphenyl)-1H,3H-furo[3,4-c]furan-1-yl]phenoxy]-1-(4-hydroxy-3-methoxyphenyl)-1,3-propanediol[a] |
| 36 | Syringaresinol |
| 37 | isolariciresinol[a] |
| 38 | icariside E4[a] |
| 39 | sakuraresinol[a] |
| 40 | 1,2-diguaiacyl-1,3-propanediol[a] |
| 41 | 2,3-dihydroxy-1-(3,4-dihydroxyphenyl)-1-propanone* |
| 42 | 2,3-dihydroxy-1-(4-hydroxy-3,5-dimethoxyphenyl)-1-propanone[a] |
| 43 | 3-Hydroxy-1-(4-hydroxy-3,5-dimethoxyphenyl)propan-1-one[a] |
| 44 | dihydroconiferyl alcohol |
| 45 | 4-acetylcatechol[a] |
| 46 | 3',4',5'-trihydroxyacetophenone[a] |
| 47 | 3,4-dihydroxy-2-methylbenzaldehyde |
| 48 | protocatechuic acid |
| 49 | 4-(dimethoxymethyl)-pyrocatechol[a] |
| 50 | Tyrosol |
| 51 | isofraxidin[a] |
| 52 | 4-hydroxycatechol[a] |
| 53 | phaseic acid[a] |

[a]First report from maple syrup
*New compounds

Preparation of Preparation of a Food-Grade Approved Extract from Maple Syrup.

According to another embodiment of the present invention, there is disclosed a food grade extract from maple tree, including maple tree parts as well as syrup (e.g. Maple Syrup-XAD extract). The generation of the extract requires the utilization of non-food grade solvents and methods, a 'food-grade approved' phenolic-enriched extract of maple syrup for future nutraceutical applications is prepared. Towards this end, the maple syrup methanol extract (MS-MeOH) may be prepared using a FDA-food grade resin, such as polymeric resins that include but are not limited to styrene and divinylbenzene resins, and styrene-divinyl-benzene (SDVB) cross-linked copolymer resin. Examples of such resins include but are not limited to Amberlite™ XAD-4 (divinylbenzene copolymer), XAD-2 (polystyrene copolymer resin), XAD-7 (aliphatic ester), XAD 7HP (aliphatic ester), XAD16 (polystyrene-divinylbenzene), XAD16HP (polystyrene-divinylbenzene), XAD761(Cross-linked phenol-formaldehyde polycondensate), XAD1180 (Polydivinylbenzene), XAD1600 (polystyrene-divinylbenzene), FPx-66 (macroreticular aromatic polymer), XFS-4257, XFS-4022 (unfunctionalized polystyrene beads), XUS-40323 and XUS-40322. Amberlite™ strong anion exchange (SAX) resin, Amberlite™ WAX Resin, a pentafluorophenyl derivatived silica gel, HLB (hydrophobic-lipophilic balanced) type SILIaPrepX phase, strong anion exchange (SAX) resin on silica or mixed-mode strong anion exchange (SAX)-$C_{18}$, an aqueous $C_{18}$ phase, a $C_{18}$ phase, a $C_{18}$ type SILIaPrepX™ phase, diatomaceous earth. According to an embodiment of the present invention, the polymeric may be Amberlite™ XAD-16 (Sigma) and adsorption chromatography is performed by adsorbing the maple syrup on the XAD-16 resin column, eluted with copious amounts of water to remove the natural sugars, then finally eluted with MeOH to yield the maple syrup methanol extract (MS-MeOH) after solvent removal in vacuo. Elution may also be effected with other solvents, which include ethanol.

1. 1 Kg of Amberlite™ XAD-16 (Sigma) soaked overnight and packed in a large glass column
2. Eluted the XAD-16 column with copious amounts of water.
3. Adsorb a certain volume (to be determined; ca. 500 mL; (make sure it is not over loaded),) of maple syrup which was previously diluted in water so that the solution is not too sticky.
4. Leave maple syrup column on XAD-16 column for ca. 1 h.
5. Elute the column with copious amounts of water to remove sugar (check the eluent for color).
6. Elute with methanol to remove phenolics.
7. Dry the methanol fraction using a rotary evaporator in vacuo, the temperature of the water bath should be set from 37° C. and should not exceed 40° C.
8. The dried sample is maple syrup XAD extract also known as MSX.
9. Repeat the steps to prepare enough quantities.

According to another embodiment, there is also disclosed a process for the extraction of polyphenolic compounds from maple syrup. The process comprises contacting an adsorbent material having a maple syrup polyphenolic fraction adsorbed thereon with an organic solvent, for a time sufficient and for a number of times sufficient, to elute and collect said maple syrup polyphenolic fraction.

According to an embodiment, the time sufficient may be about 30 minutes. The number of time sufficient is from about 1 time to about 3 times.

According to another embodiment, the maple syrup mixture is adsorbed on the adsorbent material for a time sufficient to adsorb the polyphenolic fraction on the adsorbent material, and the mixture comprises maple syrup diluted in water.

The time sufficient to adsorb said polyphenolic fraction is from about 12 to about 20 hours, or from about 12 to about 19 hours, or from about 12 to about 18 hours, or from about 12 to about 17 hours, or from about 12 to about 16 hours, or from about 12 to about 15 hours, or from about 12 to about 14 hours, or from about 12 to about 13 hours. The time sufficient to adsorb said polyphenolic fraction may be 12, 13, 14, 15, 16, 17, 18, 19, 20 hours. Preferably, the time is 16 hours.

Examples of absorbent material include but are not limited to Amberlite™ XAD-4 (divinylbenzene copolymer), XAD-2 (polystyrene copolymer resin), XAD-7 (aliphatic ester), XAD 7HP (aliphatic ester), XAD16 (polystyrene-divinylbenzene), XAD16HP (polystyrene-divinylbenzene), XAD761(Crosslinked phenol-formaldehyde polycondensate), XAD1180 (Polydivinylbenzene), XAD1600 (polystyrene-divinylbenzene), FPx-66 (macroreticular aromatic polymer), XFS-4257, XFS-4022 (unfunctionalized polystyrene beads), XUS-40323 and XUS-40322. Amberlite™ strong anion exchange (SAX) resin, Amberlite™ WAX Resin, a pentafluorophenyl derivatived silica gel, HLB (hydrophobic-lipophilic balanced) type SILIaPrepX phase, strong anion exchange (SAX) resin on silica or mixed-mode strong anion exchange (SAX)-$C_{18}$, an aqueous $C_{18}$ phase, a $C_{18}$ phase, a $C_{18}$ type SILIaPrepX™ phase, diatomaceous earth.

According to another embodiment, the process may further comprise the step of diluting the maple syrup in water prior prior to adsorption on said adsorbent material.

According to another embodiment, the process may further comprise the step of washing the adsorbent material with water prior to step a).

According to another embodiment, the process may further comprise step b): heating the collected polyphenolic fraction to evaporate the organic solvent and obtain a dried polyphenolic fraction. Heating may be at a temperature of about 37° C. to about 40° C.

According to another embodiment, the organic solvents suitable for the process of the present invention may be chosen from methanol, ethyl acetate, butanol, ethanol, methyl tert-butyl ether, and combinations thereof.

According to yet another embodiment, the process of the present invention may further comprise prior to step a) an extraction with a mixture of solids for extraction of a sugar from said maple syrup. For example, such extraction with a mixture of solids comprises extraction with $MgSO_4$, NaCl, and a solid absorbent. Preferably, the solid absorbent for this extraction may be chosen from an aminated silica resin, a $C_{18}$ silica resin, or combinations thereof.

According to yet another embodiment, the process of the present invention may further comprising prior to step a) a liquid-liquid extraction of the maple syrup. For example, the liquid-liquid extraction may comprise an ethyl acetate extraction, a butanol extraction, or combinations thereof, followed by adsorption on a silicon dioxide ($SiO_2$)/magnesium oxide (MgO) solid phase having a ratio of about 85% $SiO_2$ and about 15% MgO (Florisil®).

According to yet another embodiment, there is disclosed an extract obtained from the process of the present invention.

Preparation of Maple Syrup Butanol Extract without Sugar (MS-BuOH without Sugar)

According to another embodiment of the present invention, there is disclosed an MS butanol extract without sugar.

1. A known volume of maple syrup (based on the size of your separatory funnel) is subjected to liquid-liquid partitioning with n-butanol (1:1 v/v; 3 times). The maple syrup is diluted with water before partitioning since it is too sticky. (Usually we add around 300 ml water to 1 L maple syrup).

2. Combine the butanol fraction and dry in vacuo as previously described.

3. The dried butanol fraction will be still very sticky and we usually freeze-dry or vacuum dry to make sure it has a powdery consistency 4. The dried butanol extract powder is reconstituted in methanol and the filtered to remove the white solid i.e. sugars. The liquid portion is part is dried in vacuo as previously described.

5. After removing the solvent from the liquid part, add certain methanol to remove sugar again. Repeat filtering and drying.

6. The final dried extract is the MS-BuOH extract without sugar.

7. Repeat steps to prepare enough quantities

Preparation of Maple Syrup Butanol Extract with Sugar (MS-BuOH with Sugar)

According to another embodiment of the present invention, there is disclosed an MS butanol extract without sugar.

Follow steps 1-3 above. In this case, the sugars are not removed with methanol.

Determination of Total Phenolic Content by the Folin-Ciocalteu Method

The total phenolic contents of the maple syrup extracts are determined according to the Folin-Ciocalteu method and is measured as gallic acid equivalents (GAEs). Briefly, the extracts were diluted 1:100 with methanol/$H_2O$ (1:1, v/v), and 200 µL of each sample was incubated with 3 mL of methanol/$H_2O$ (1:1, v/v) and 200 µL of Folin-Ciocalteu reagent for 10 min at 25° C. After this, 600 µL of 20% $Na_2CO_3$ solution was added to each tube and vortexed. Tubes were further incubated for 20 min at 40° C. and after, incubation; samples were immediately cooled in an ice bath to room temperature. Samples and standard (gallic acid) were processed identically. The absorbance was determined at 755 nm, and final results were calculated from the standard curve obtained from a Spectramax plate reader.

Methods of Solvent Removal

According to some embodiments, solvent removal from the extracts of the present invention may be effected in vacuo. However, other known techniques may be employed, such as atomization, lyophilization, evaporation, crystallization, dehydration, precipitation, centrifugation, or any other suitable process to eliminate the aqueous phase from any of the extracts of the present invention.

TABLE 5

Presence and relative levels of pure isolated phenolic compounds in the different maple syrup extracts*

| Compound | Name | MS-BuOH | MS-EtOAc | MS-MeOH |
|---|---|---|---|---|
| 1 | Lyoniresinol | + | + | + |
| 2 | Secoisolariciresinol | + | + | + |
| 3 | 2,3-dihydro-3-(hydroxymethyl)-2-(4-hydroxy-3-methoxyphenyl)-7-methoxy-5-benzofuranpropanol (dihydrodehydrodiconiferyl alcohol) | + | | + |
| 4 | 5'-methoxydehydroconiferyl alcohol | + | | |

TABLE 5-continued

Presence and relative levels of pure isolated phenolic compounds in the different maple syrup extracts*

| Compound | Name | MS-BuOH | MS-EtOAc | MS-MeOH |
|---|---|---|---|---|
| 5 | 1,3-propanediol, 1-(4-hydroxy-3-methoxyphenyl)-2-[4-[(1E)-3-hydroxy-1-propenyl]-2-methoxyphenoxy]-, (1R,2R) | + |  | + |
| 6 | 1-(4-hydroxy-3-methoxyphenyl)-2-[4-(3-hydroxypropyl)-2-methoxyphenoxy]-propane-1,3-diol (guaiacylglycerol-β-O-4'-dihydroconiferyl alcohol) | + | + | + |
| 7 | 3-[(4-[(6-dexoy-α-L-mannopyranosyl)oxy]-3-methoxyphenyl)-5-(3,4-dimethoxyphenyl)dihydro-3-hydroxy-4-(hydroxymethyl)-2(3H)-furanone | + |  | + |
| 8 | Scopoletin | + | + | + |
| 9 | Fraxetin | + |  | + |
| 10 | (E)-3,3'-dimethoxy-4,4'-dihydroxy stilbene | + |  | + |
| 11 | 2-Hydroxy-3',4'-dihydroxyacetophenone | + |  | + |
| 12 | 1-(2,3,4-trihydroxy-5-methylphenyl)-ethanone | + |  | + |
| 13 | 2,4,5-trihydroxyacetophenone | + |  |  |
| 14 | Catechaldehyde | + |  | + |
| 15 | Vanillin | + | + | + |
| 16 | Syringaldehyde | + |  | + |
| 17 | Gallic acid | + |  | + |
| 18 | trimethyl gallic acid methyl ester | + |  |  |
| 19 | Syringic acid | + | + | + |
| 20 | Syringenin | + |  | + |
| 21 | (E)-coniferyl alcohol (coniferol) | + |  | + |
| 22 | C-veratroylglycol | + | + | + |
| 23 | 1,2-benzenediol (catechol) | + |  | + |
| 24 | 5-(3",4"-dimethoxyphenyl)-3-hydroxy-3-(4'-hydroxy-3'-methoxybenzyl)-4-hydroxymethyl-dihydrofuran-2-one |  | + | + |
| 25 | (erythro, erythro)-1-[4-[2-hydroxy-2-(4-hydroxy-3-methoxyphenyl)-1-(hydroxymethyl)ethoxy]-3,5-dimethoxyphenyl]-1,2,3-propanetriol |  | + | + |
| 26 | (erythro, threo)-1-[4-[2-hydroxy-2-(4-hydroxy-3-methoxyphenyl)-1-(hydroxymethyl)ethoxy]-3,5-dimethoxyphenyl]-1,2,3-propanetriol |  | + | + |
| 27 | (threo, erythro) 1-[4-[(1R,2R)-2-hydroxy-2-(4-hydroxy-3-methoxyphenyl)-1-(hydroxymethyl)ethoxy]-3-methoxyphenyl]-1,2,3-propanetriol |  | + | + |
| 28 | (threo, threo) 1-[4-[(1R,2R)-2-hydroxy-2-(4-hydroxy-3-methoxyphenyl)-1-(hydroxymethyl)ethoxy]-3-methoxyphenyl]-1,2,3-propanetriol |  | + | + |
| 29 | Threo-guaiacylglycerol-β-O-4'-dihydroconiferyl alcohol |  | + | + |
| 30 | erythro-1-(4-hydroxy-3-methoxyphenyl)-2-[4-(3-hydroxypropyl)-2,6-dimethoxyphenoxy]-1,3-propanediol |  | + |  |
| 31 | 2-[4-[(2S,3R)-2,3-dihydro-3-(hydroxymethyl)-5-(3-hydroxy propyl)-7-methoxy-2-benzofuranyl]-2,6-dimethoxyphenoxy]-1-(4-hydroxy-3-methoxyphenyl)-1,3-propanediol |  | + | + |
| 32 | Acernikol |  | + | + |
| 33 | Leptolepisol D |  | + | + |
| 34 | Buddenol E |  | + | + |
| 35 | (1S,2R)-2-[2,6-dimethoxy-4-[(1S,3aR,4S,6aR)-tetrahydro-4-(4-hydroxy-3,5-dimethoxyphenyl)-1H,3H-furo[3,4-c]furan-1-yl]phenoxy]-1-(4-hydroxy-3-methoxyphenyl)-1,3-propanediol |  | + | + |
| 36 | Syringaresinol |  | + | + |
| 37 | Isolariciresinol |  | + | + |
| 38 | Icariside E4 |  | + | + |
| 39 | Sakuraresinol |  | + | + |
| 40 | 1,2-diguaiacyl-1,3-propanediol |  | + | + |
| 41 | 2,3-dihydroxy-1-(3,4-dihydroxyphenyl)-1-propanone |  | + | + |
| 42 | 2,3-dihydroxy-1-(4-hydroxy-3,5-dimethoxyphenyl)-1-propanone |  | + | + |
| 43 | 3-hydroxy-1-(4-hydroxy-3,5-dimethoxyphenyl)propan-1-one |  | + | + |
| 44 | Dihydroconiferyl alcohol |  | + | + |
| 45 | 4-hydroxycatechol |  | + | + |
| 46 | 3',4',5'-Trihydroxyacetophenone |  | + | + |
| 47 | 3,4-dihydroxy-2-methylbenzaldehyde |  | + |  |
| 48 | Protocatechuic acid |  | + | + |
| 49 | 4-(dimethoxymethyl)-pyrocatechol |  | + | + |

TABLE 5-continued

Presence and relative levels of pure isolated phenolic compounds in the different maple syrup extracts*

| Compound | Name | MS-BuOH | MS-EtOAc | MS-MeOH |
| --- | --- | --- | --- | --- |
| 50 | Tyrosol | | + | + |
| 51 | Isofraxidin | | + | + |
| 52 | 4-acetylcatechol | | + | + |
| 53 | phaseic acid | | + | |
| 54 | Quebecol | + | | |
| 55 | Ferulic acid | | | + |
| 56 | p-coumaric acid | | | + |
| 57 | Catechin | | | + |
| 58 | Epicatechin | | | + |

The present invention will be more readily understood by referring to the following examples which are given to illustrate the invention rather than to limit its scope.

Example 1

Assessment of Metabolic Syndrome-Preventing Effects of the Nutriprotective Diet

The objective of the current example is to evaluate the metabolic syndrome-improving effects of the nutriprotective diet.

Materials and Methods

A maple syrup extract is used which has been prepared from the amber grade of maple syrup by treatment with n-butanol which may be useful to prepare an extremely low-sugar product. A total amount of 50 g butanol extract, 20 mg butanol extract basis, is necessary for 5 repetitions of a 60-day-feeding trial with 8 rats fed on 20 g diet/capita/day.

Feeding

Male rats (Wistar) are fed on an AIN93G-based high-fat diet with 0.1% butanol extract of maple syrup (n=8) or on the same diet without the extract (n=8) for 2 months. During the feeding, daily body weight gains and diet intakes are measured every day.

Dissection

Each rat after the feeding is subjected to dissection for sampling the systemic blood, small-intestinal epithelia, liver and adipose tissue.

Blood Chemistry Analysis

Systemic blood qualities are analyzed for 20-50 items.

Genomics

Transcriptomics is carried with for total RNA samples from each organ or tissue by DNA microarray analysis using affymetrix gene chip.

Results

The use of the butanol extract of maple syrup as a supplement to high-fat (or high-colorie) diets reduces the risk of metabolic syndromes by modulating the lipid and/or sugar metabolic pathways.

Example 2

Figure 8:
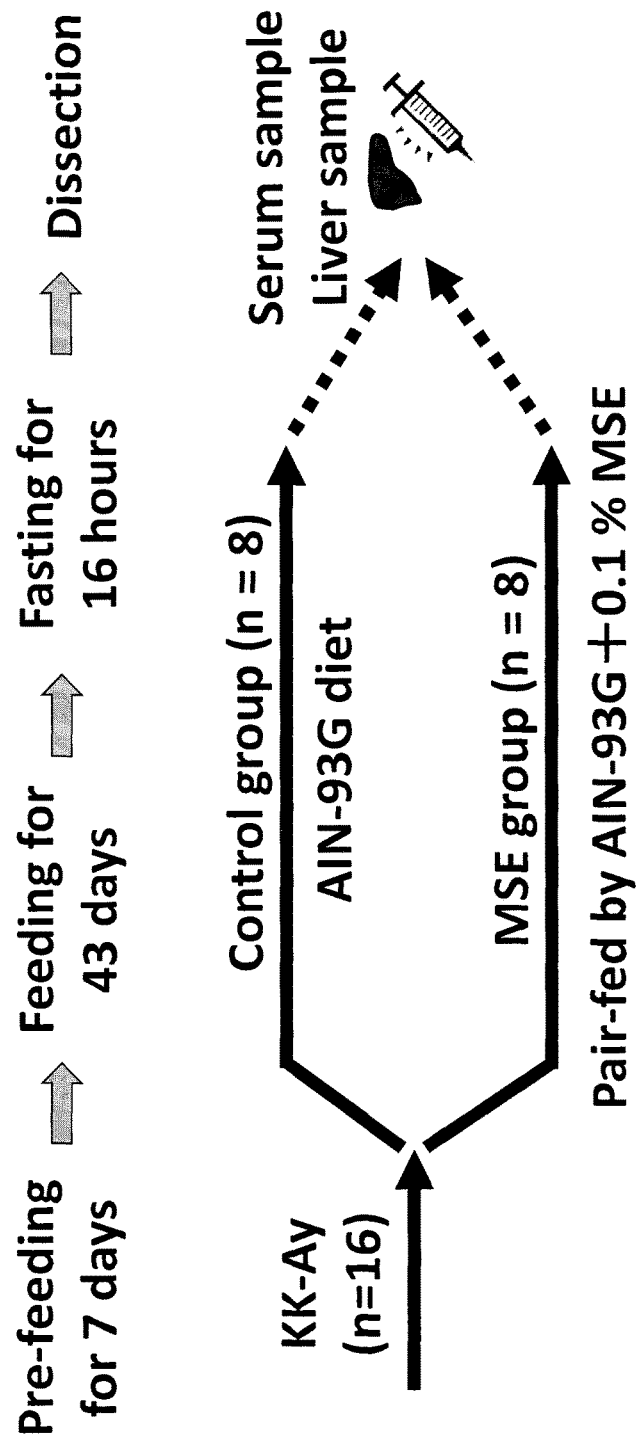
FIG. 8 illustrates the experimental design of a study described herein.

Global Analysis of Hepatic Gene Expression Profiles in Diabetes Model KK-AY Mice Now referring to FIG. 8, the purpose of this study is to elucidate the effect of butanol extract of maple syrup (MSE, as described above) on the liver of T2DM model mice— KK-Ay mice (diabetic mice). Male KK-Ay mice, aged 4 weeks, as T2DM model mice for investigation of obesity, hyperglycemia and insulin resistance are selected and separated into two experimental groups as shown in FIG. 8: 16 males, control group (n=8) fed AIN-93G diet, and experimental group (N=8) fed MSE (AIN-93G diet+0.1% MSE). The animals are prefed the same normal diet for 7 days, then fed the experimental diets for 43 days. They are fasted for 16 hours and liver and serum samples are collected.

Figure 9:
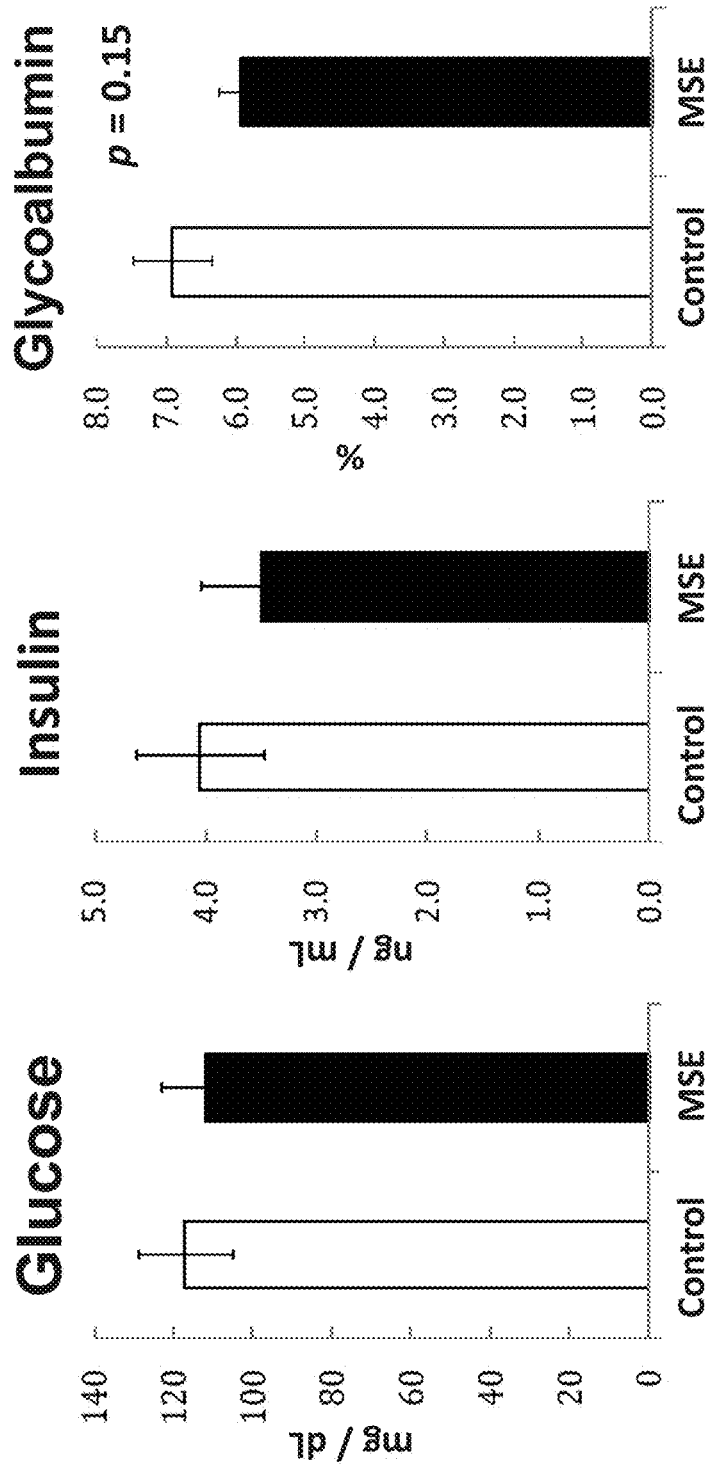
FIG. 9 illustrates biochemical measurements analysis of a study described herein.
Figure 10:
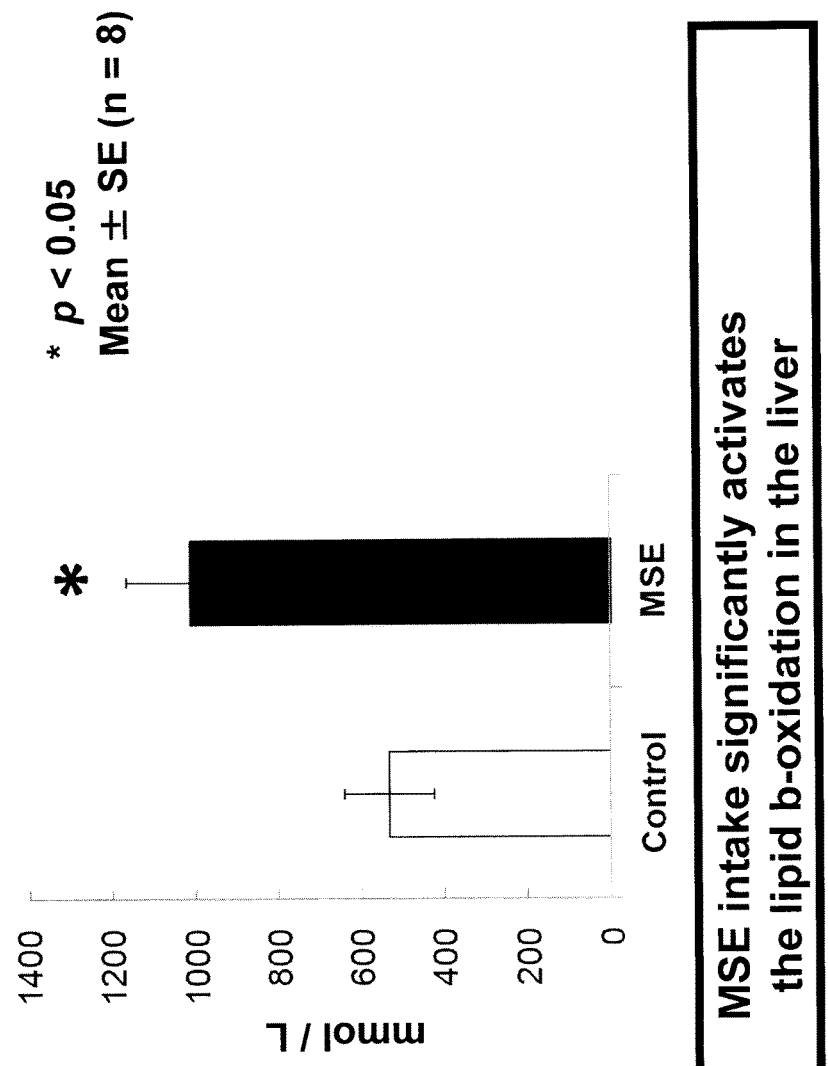
FIG. 10 illustrates biochemical measurements analysis of a study described herein.
Figure 11:
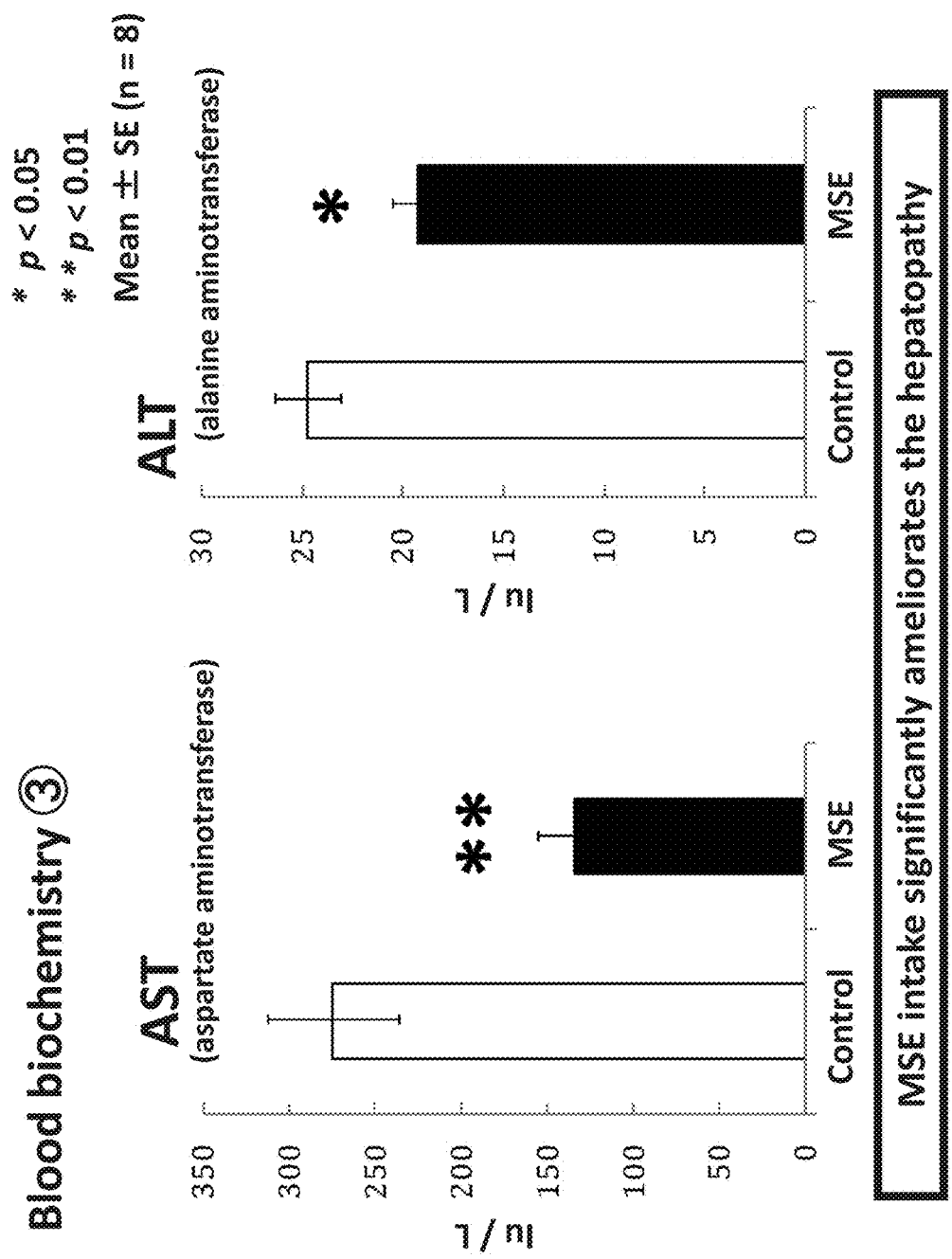
FIG. 11 illustrates biochemical measurements analysis of a study described herein.

Now referring to FIGS. 9 to 11. Measurement of serum glucose, insulin and glycoalbumin levels show that MSE intake tends to improve hyperglycemia (FIG. 9). Furthermore, as shown in FIG. 10, MSE intake significantly activates the lipid b-oxidation in the liver, resulting in increased concentration of total ketone bodies. Furthermore, as shown by the measurement of the activity of aspartate aminotransferase (AST) and alanine aminotransferase (ALT) (FIG. 11), MSE intake significantly ($p<0.01$ and $p<0.05$ respectively) ameliorates hepatopathy.

Figure 12:
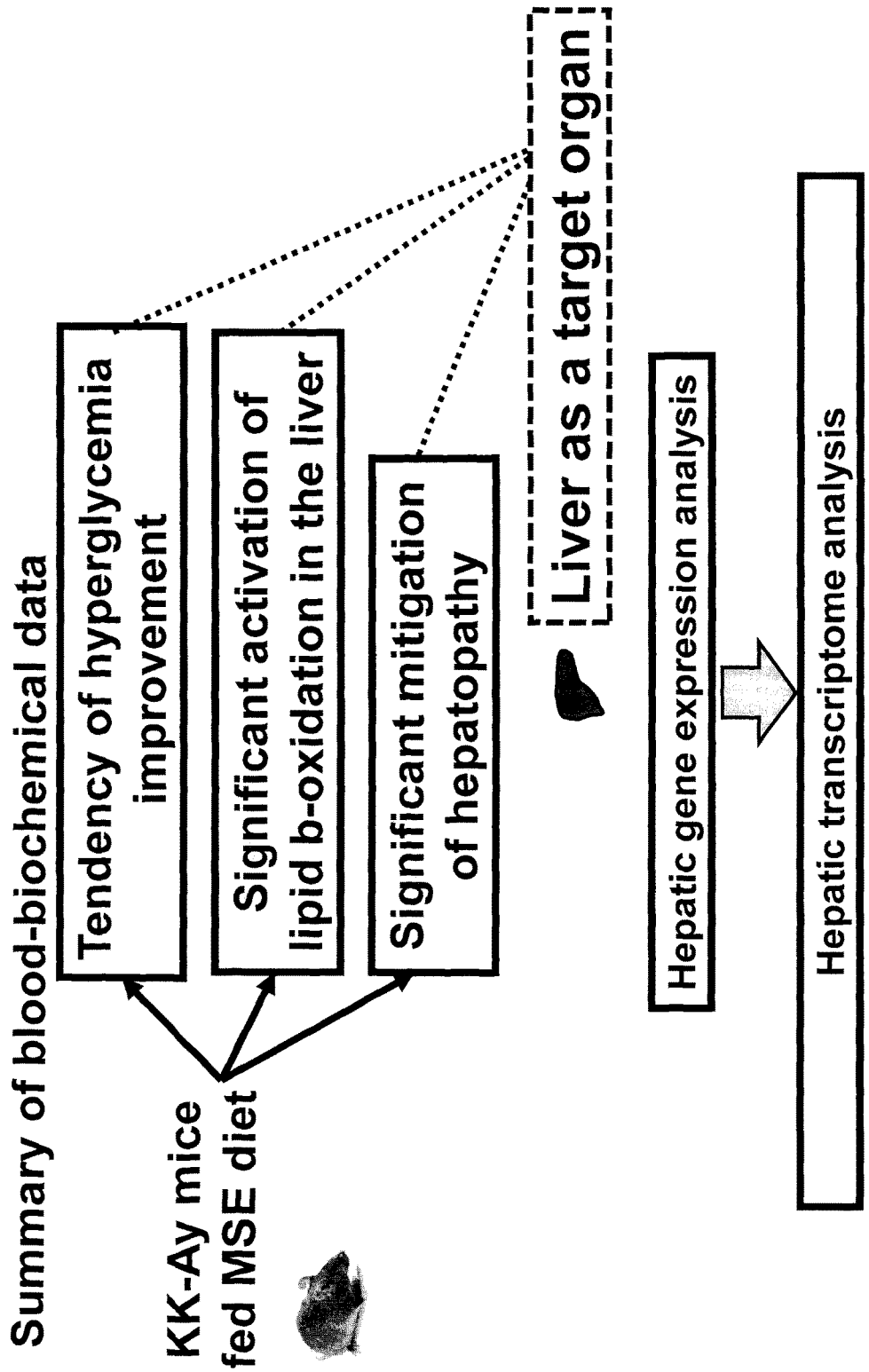
FIG. 12 illustrates a summary of the biochemical measurements analysis of a study described herein.

As summarized in FIG. 12, feeding of MSE to KK-Ay mice results in improved hyperglycemia, activation of beta-oxidation, and mitigation of hepatopathy.

Figure 13:
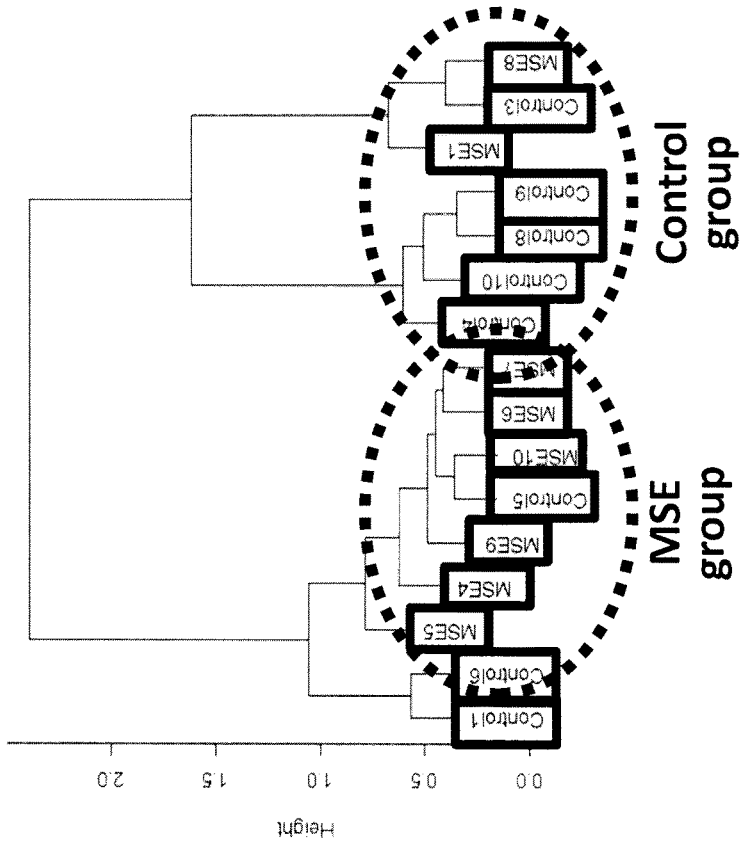
FIG. 13 illustrates the data of a DNA microarray analysis described herein.
Figure 14:
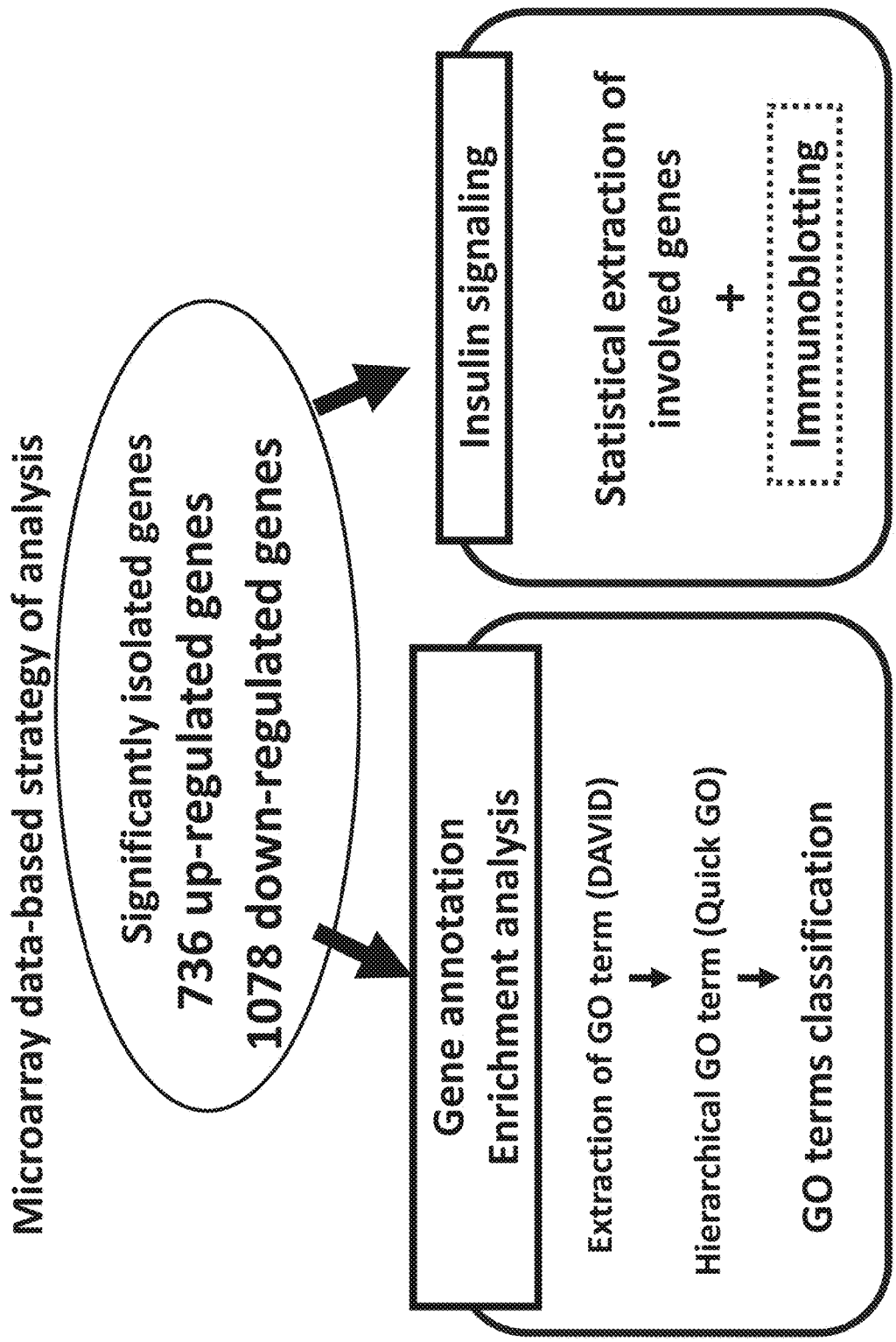
FIG. 14 illustrates the analysis strategy of a microarray analysis described herein.
Figure 15:
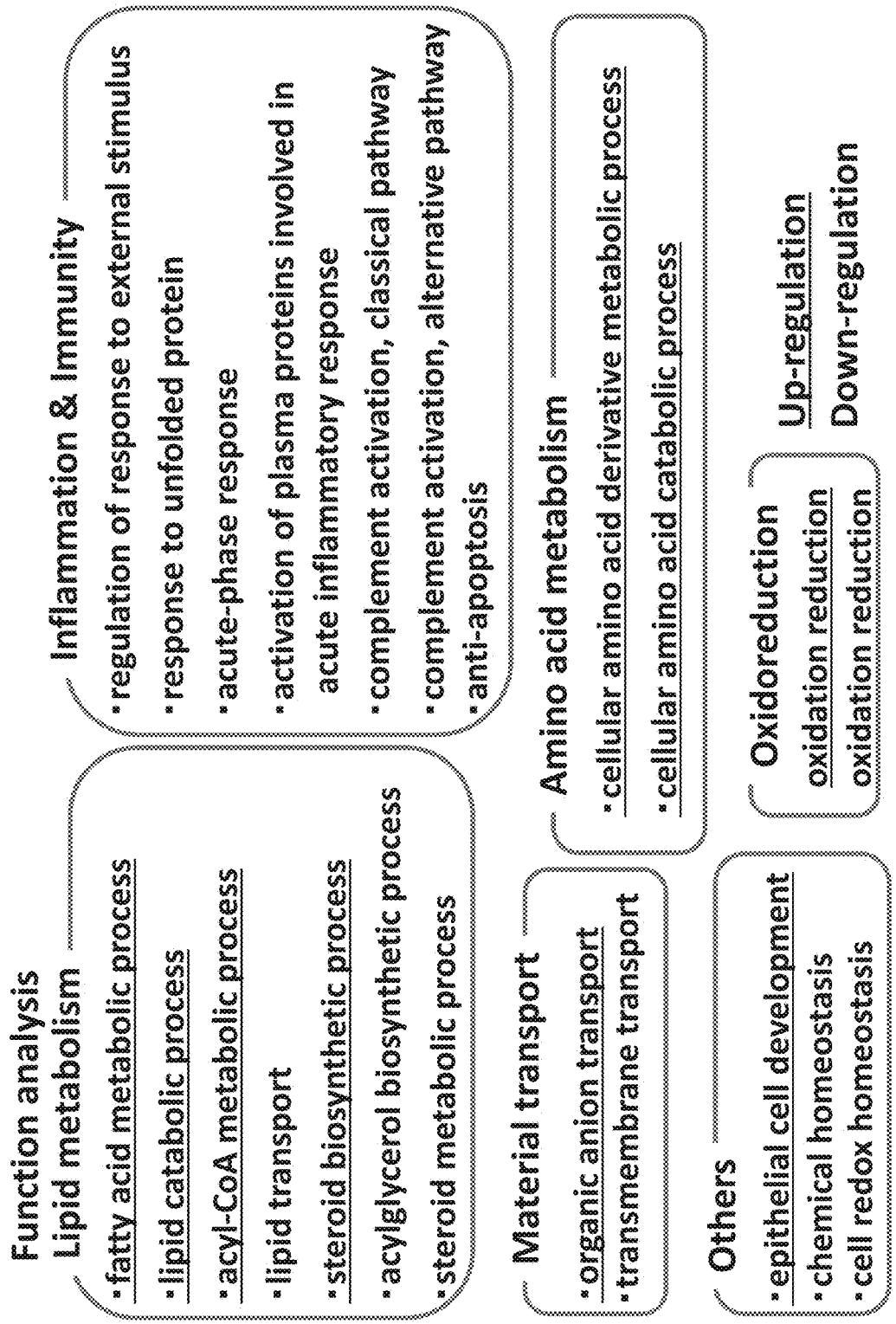
FIG. 15 illustrates the functional analysis of the microarray analysis described herein.

Next, hepatic transcriptome analysis is performed with Affymetrix Genechip (Mouse Genome 430 2.0). Microarrays are performed and results are normalized with the distribution free weighted method (DFW). The two experimental groups clustered separately from one another (FIG. 13)., indicating that there are noticeable differences in gene expression between the two groups. Furthermore, there are 736 significantly up-regulated genes and 1078 significantly down-regulated genes in the MSE group (FDR<0.05).

The significantly differentially expressed genes are then analyzed by gene annotation enrichment analysis, and insulin signaling is focussed on by verifying the statistical significance of the genes of this signalling pathway, as well as by immunoblotting.

Figure 16:
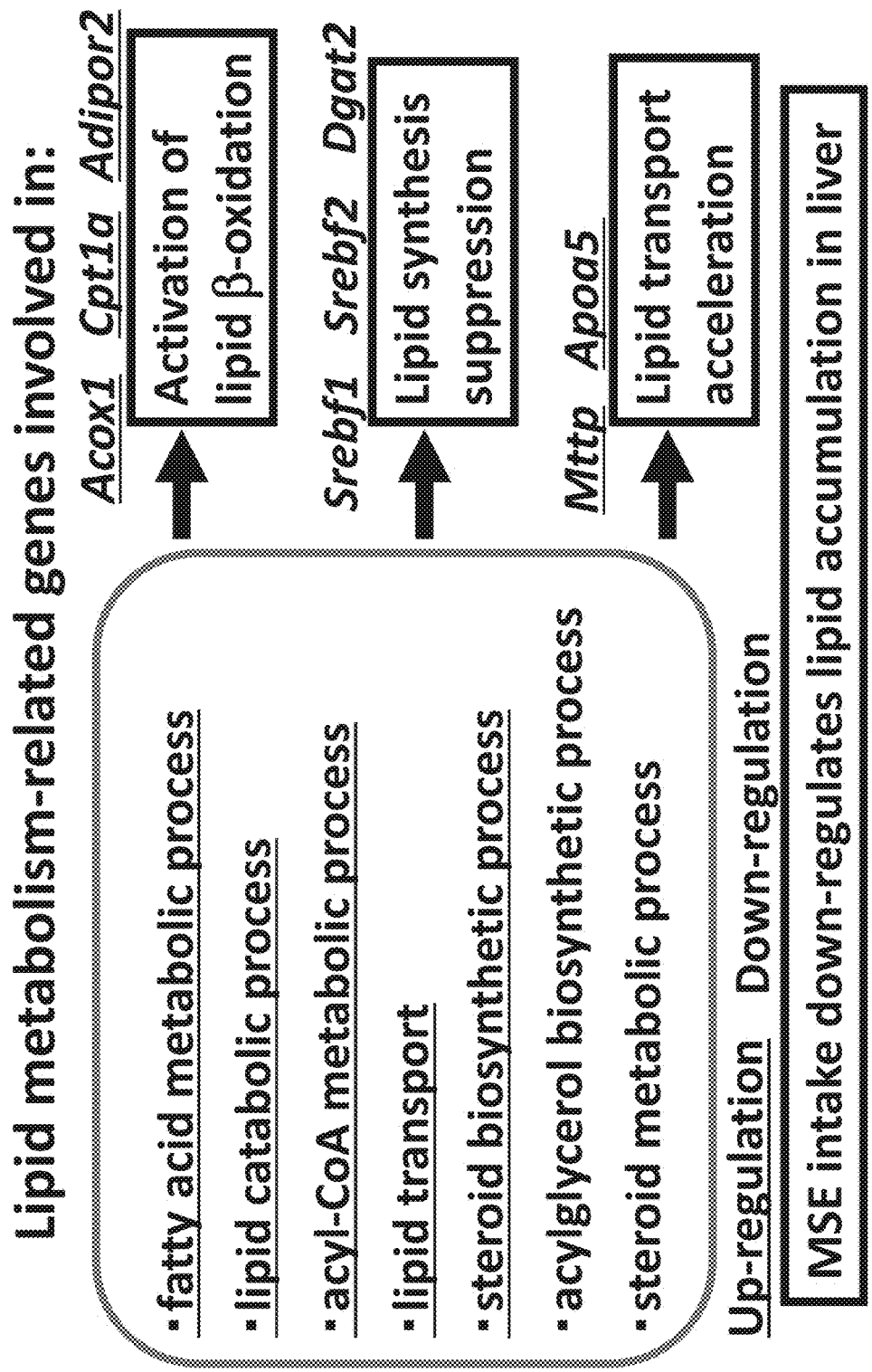
FIG. 16 illustrates the lipid metabolism-related genes observed in the analysis described herein.
Figure 17:
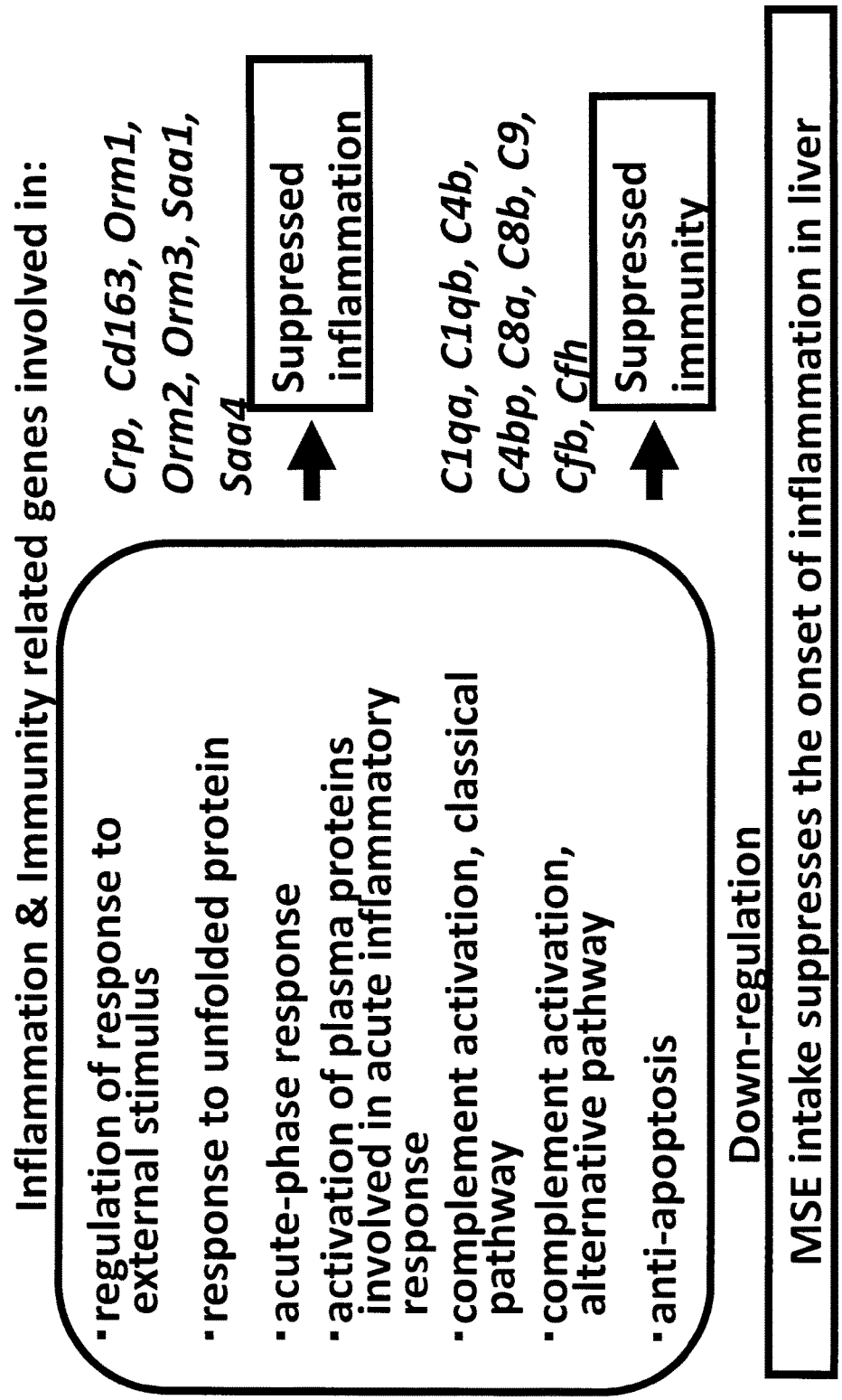
FIG. 17 illustrates the inflammation and immunity related genes observed in the analysis described herein.
Figure 18:
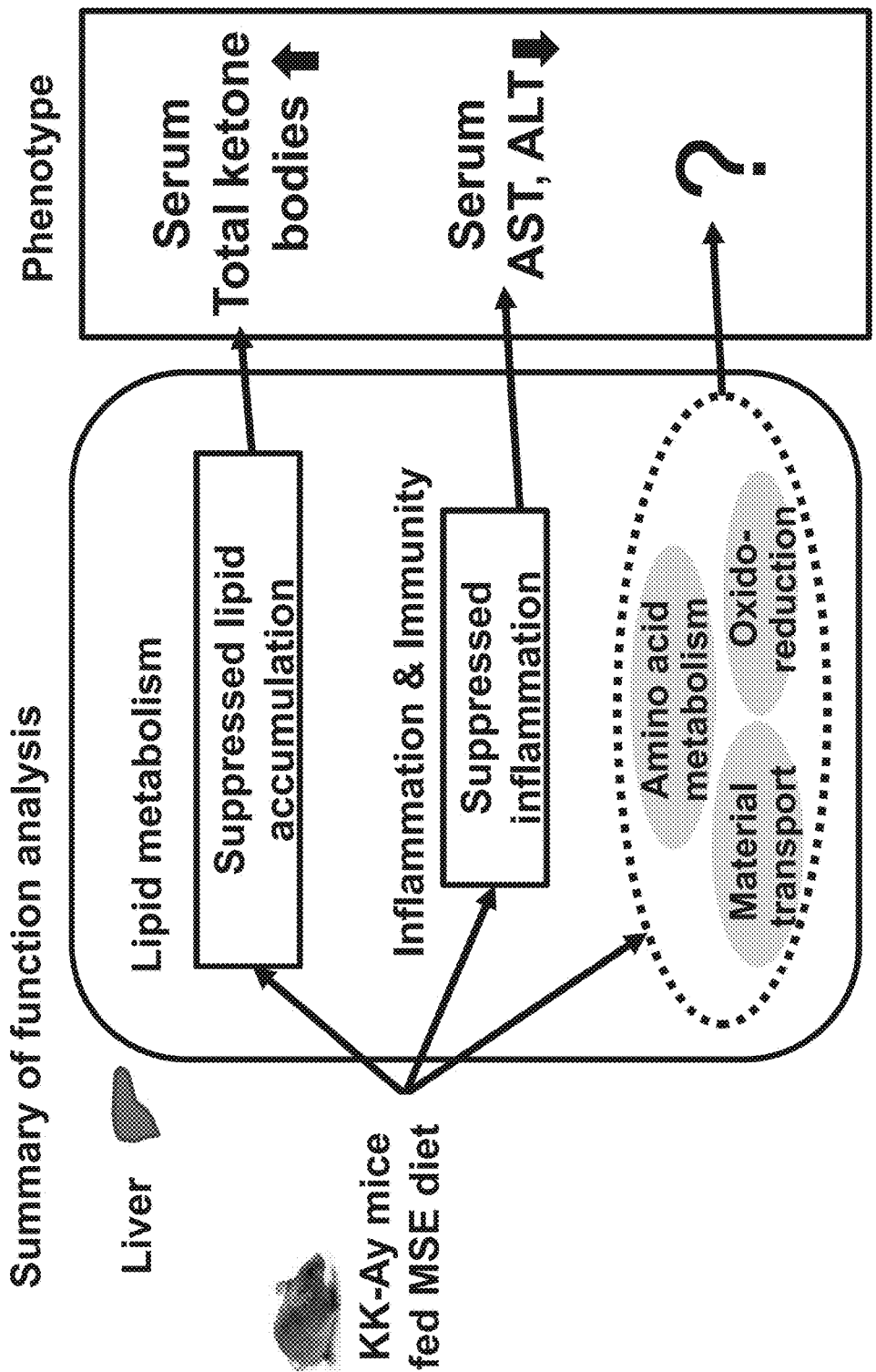
FIG. 18 illustrates a summary of the functional analysis performed herein.

With respect to gene annotation enrichment analysis, as shown in FIGS. 15 to 18, the results show significant changes in lipid metabolism, inflammation and immunity, material transport, amino acid metabolism, oxidoreduction, as well as epithelial cell development, chemical homeostasis, and cell redox homeostasis. With respect to lipid metabolism-related genes, MSE intake appears to down-regulate lipid accumulation in the liver (FIG. 16). With respect to inflammation and immunity related genes, MSE appears to suppress the onset of inflammation in the liver (FIG. 17). As summarized in FIG. 18, the suppression of lipid accumulation in the liver is consistent with an increase in the total ketone bodies in serum, while the suppression of inflammation is consistent with reduction is serum AST and ALT.

Figure 19:
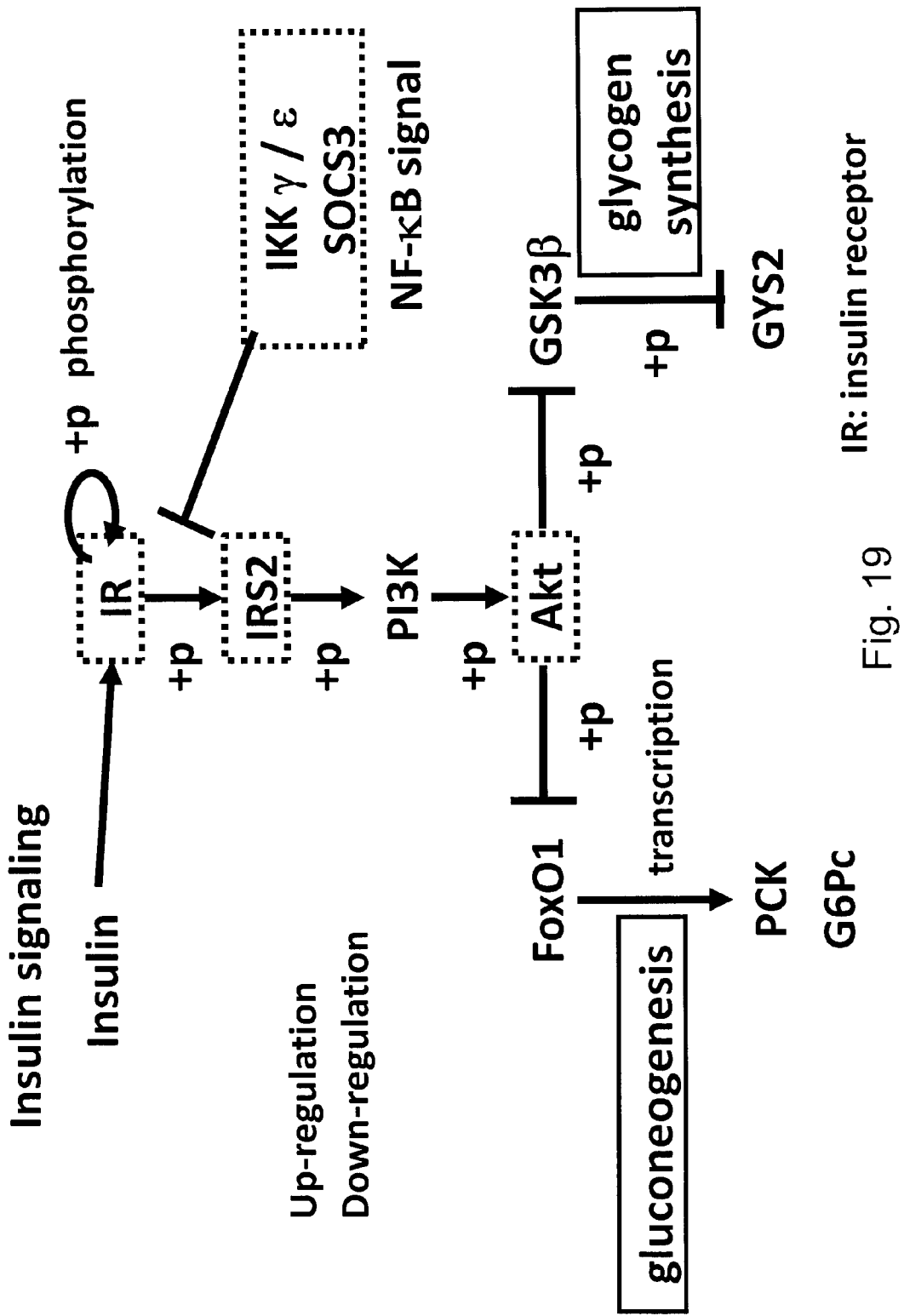
FIG. 19 illustrates the effect of a MSE diet on the insulin signaling pathway.
Figure 20:
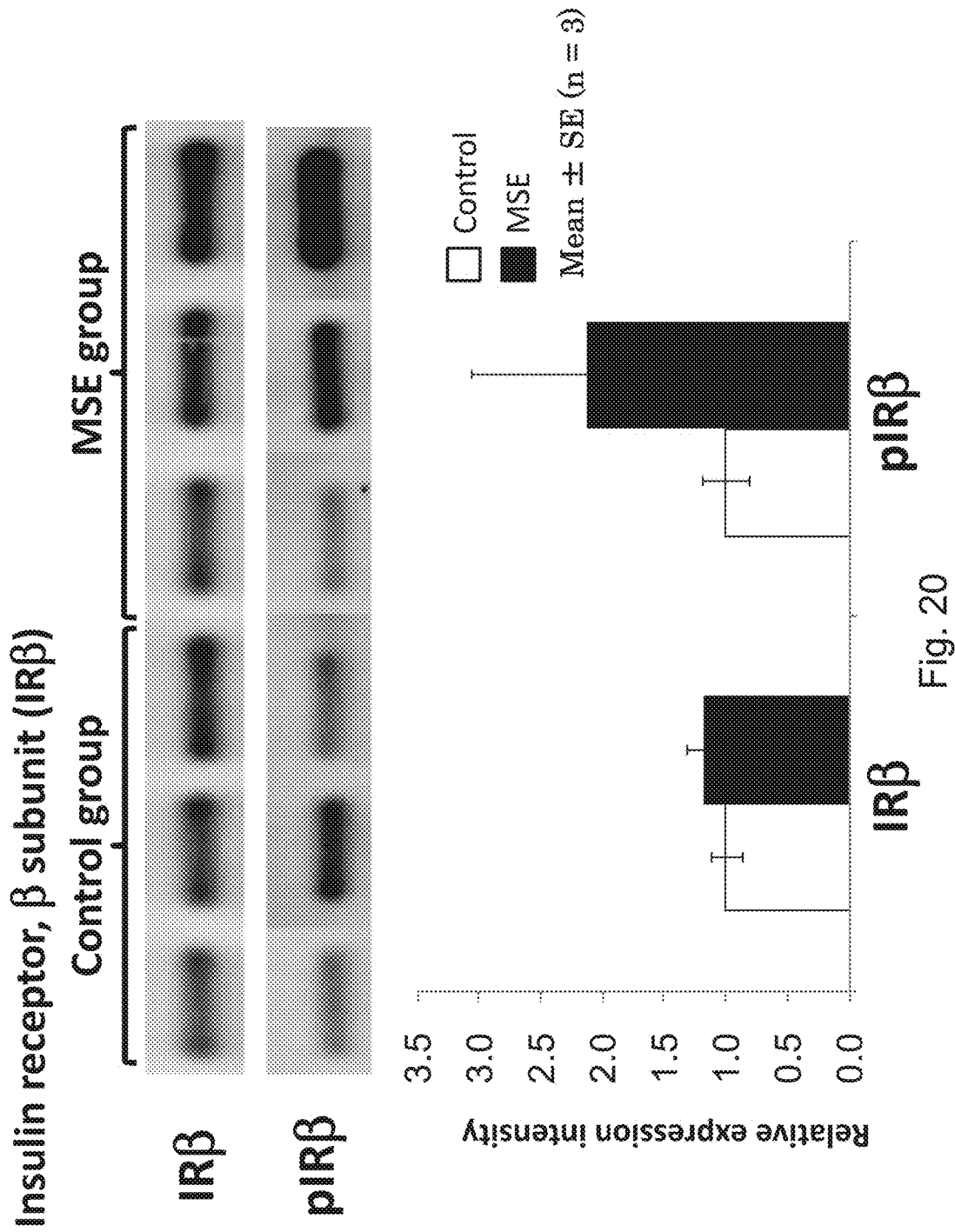
FIG. 20 illustrates the effect of MSE on the insulin receptor beta subunit.
Figure 21:
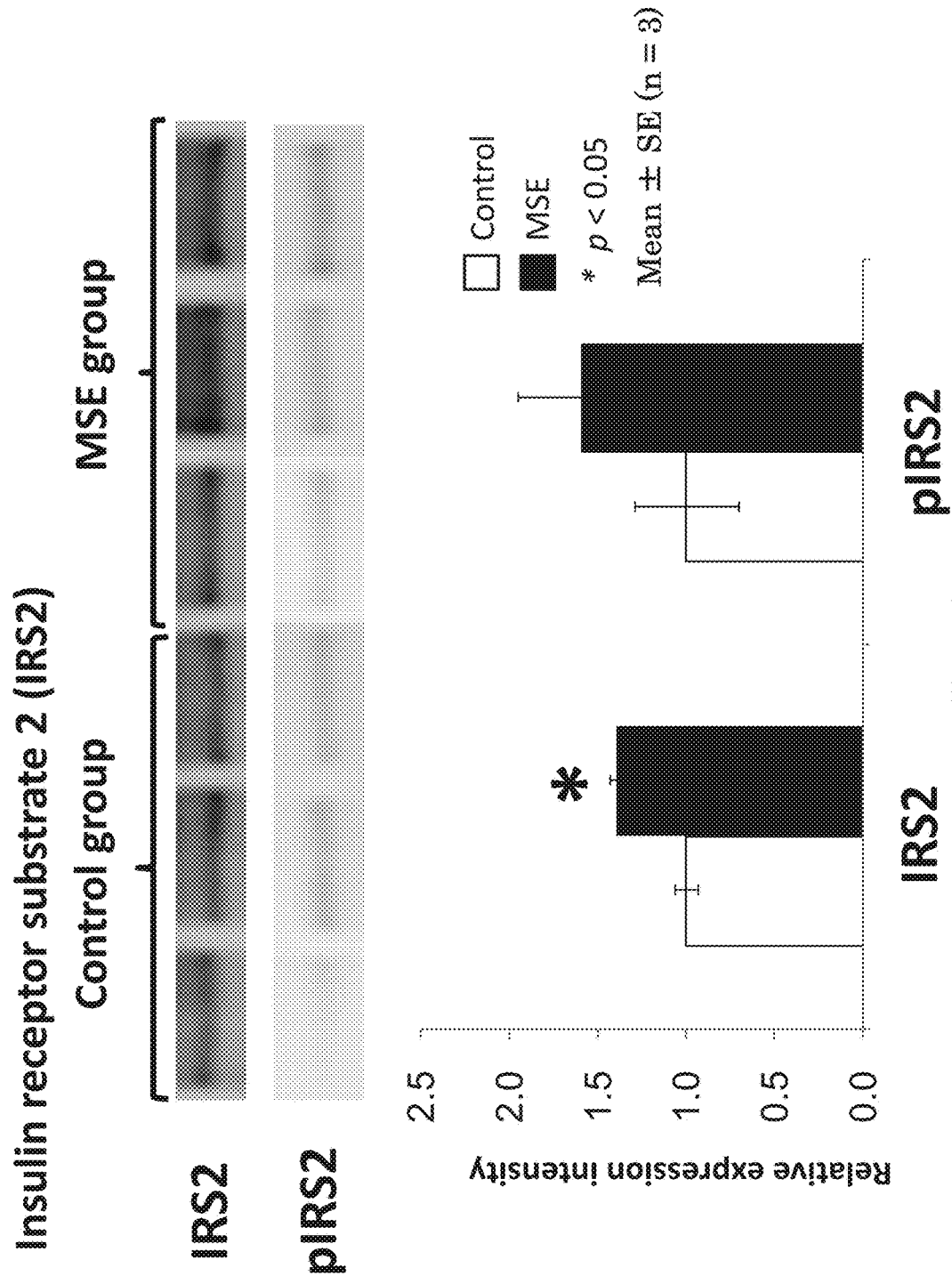
FIG. 21 illustrates the effect of MSE on the insulin receptor substrate 2.
Figure 22:
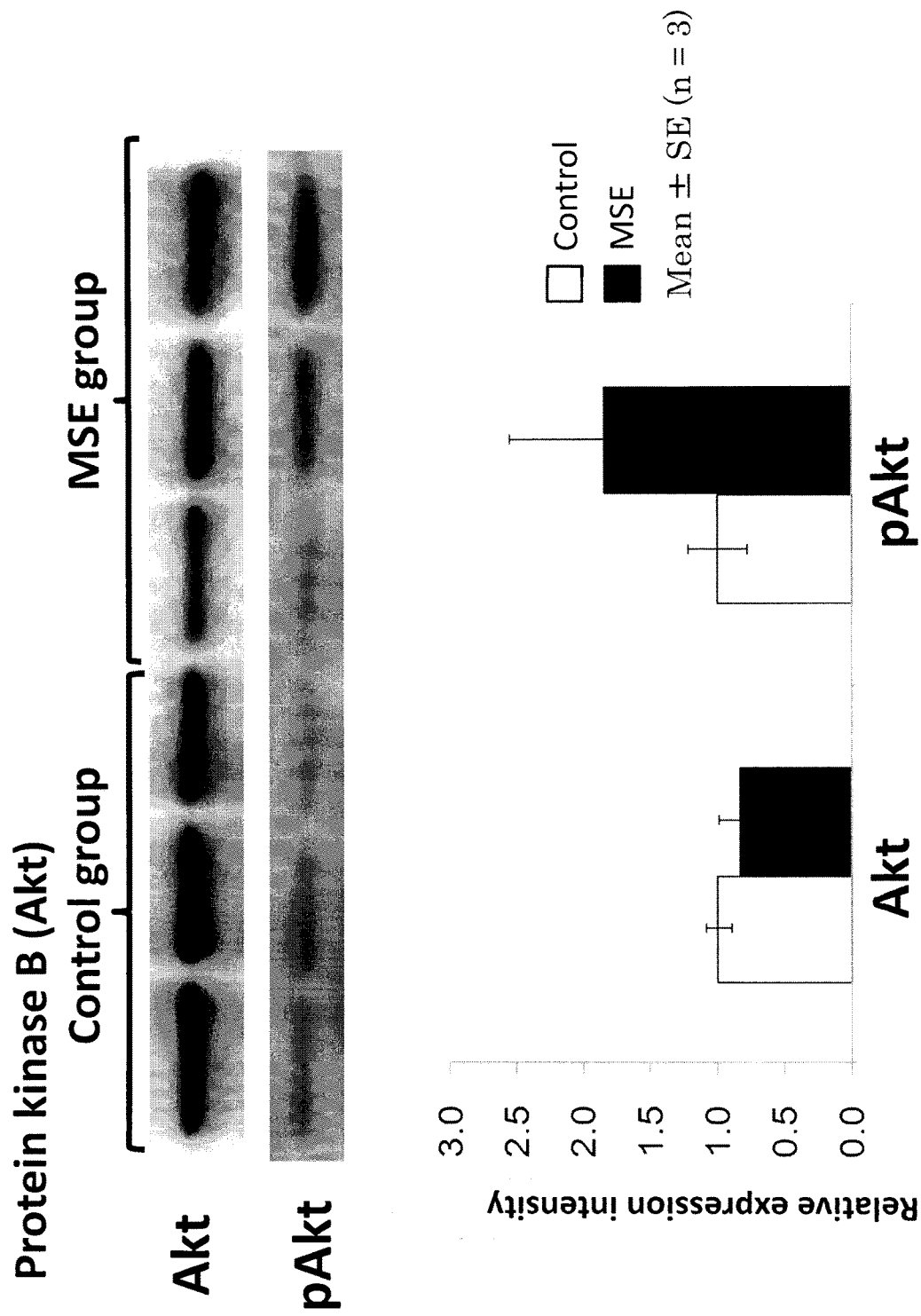
FIG. 22 illustrates the effect of MSE on the protein kinase B (Akt).
Figure 23:
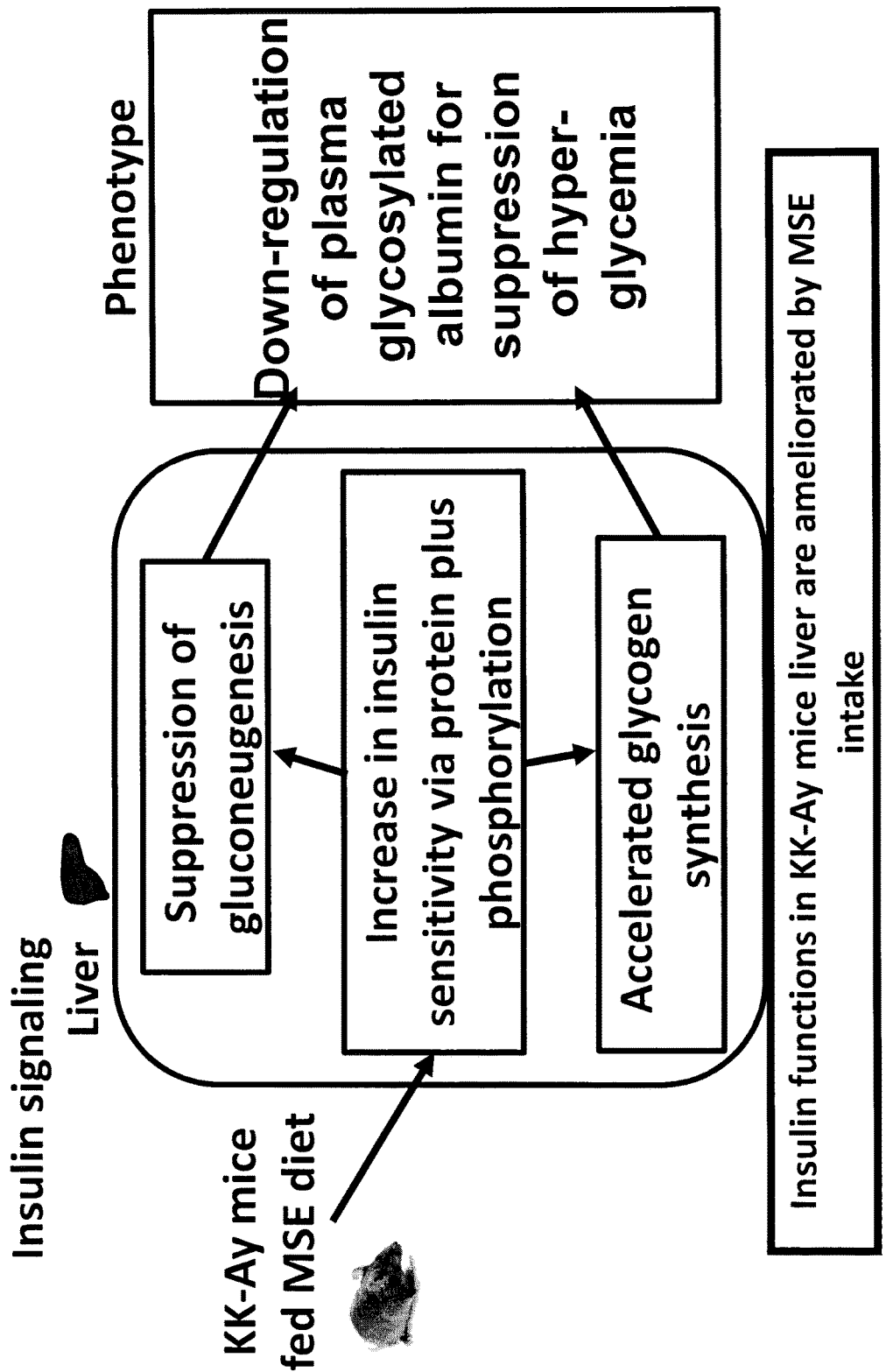
FIG. 23 illustrates a summary of the effect of MSE on liver signaling and the associated phenotypes.
Figure 24:
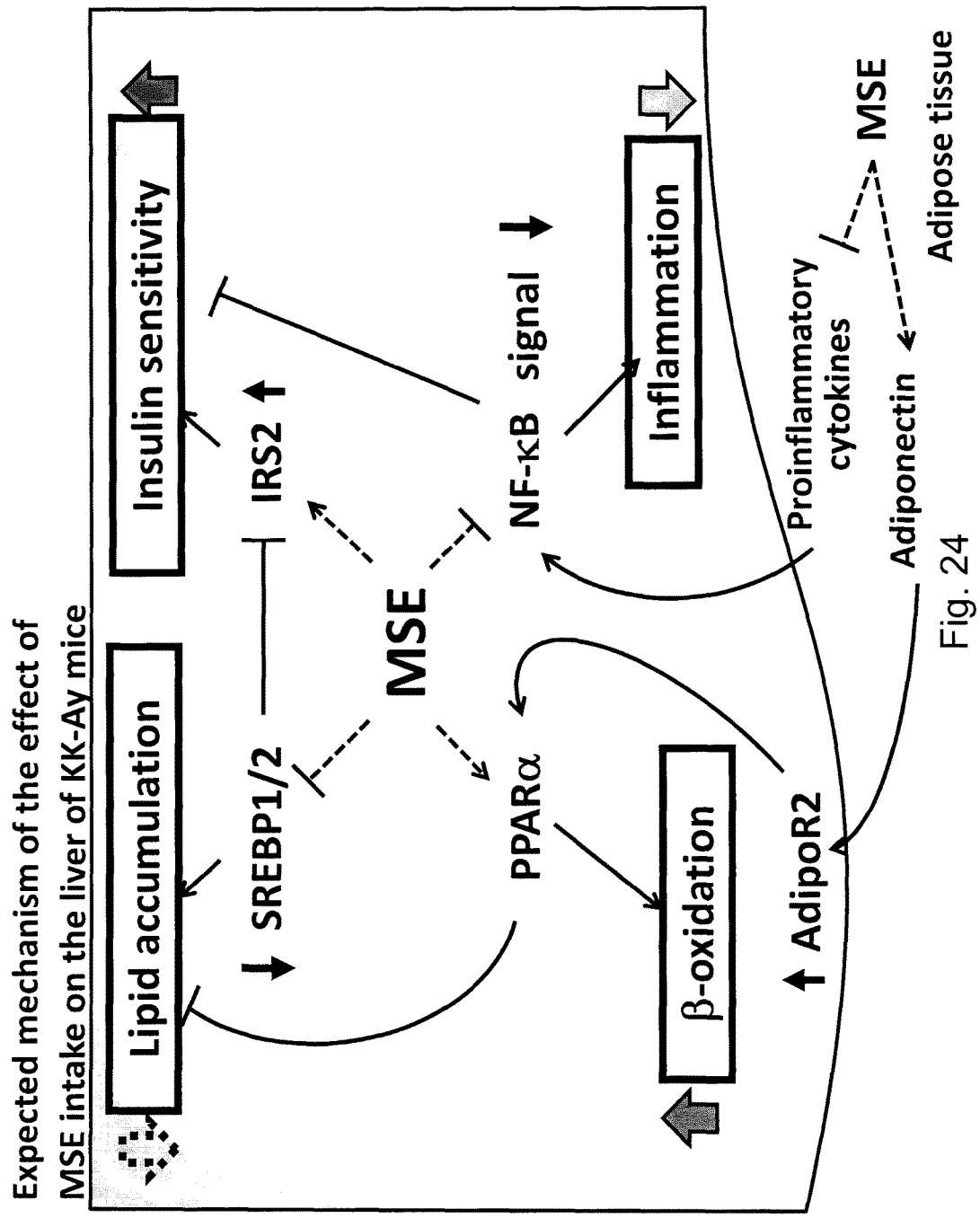
FIG. 24 illustrates the expected mechanism of action of the effect of MSE intake on liver metabolism of KK-Ay mice.

Next, as shown in FIGS. 19 to 24 the insulin signalling pathway is analyzed (FIG. 19). Immunoblotting of insulin receptor and phospho-insulin receptor (IR) beta subunit in each group reveals an increase in phosphorylation of the insulin receptor beta subunit (FIG. 20). Immunoblotting of the insulin receptor substrate 2 (IRS2) reveals an increase in protein expression of IRS2 in MSE treated animals. Immunoblotting of the protein kinase B (Akt) protein and phosphoprotein revealed an increase phosphorylated Atk in the MSE treated group (FIG. 22). As shown in FIG. 23, MSE intake by KK-Ay mice lead to an overall improvement of the insulin signalling function of KK-Ay mice liver. This result is consistent with the observed downregulation of plasma glycosylated albumin for suppression of hyperglycemia. As shown in FIG. 24, the suggested mechanism of the effect of MSE on the liver of KK-Ay mice is through decrease lipid accumulation, improved insulin sensitivity, increased β-oxidationm and decreased inflammation.

Example 3

Assessment of Metabolic Syndrome-Preventing Effects of a Maple Syrup Extract Supplemented High-Fat Diet Now referring to FIGS. 25 to 31, the aim of this study is to clarify the liver-protecting effect of maple syrup using mice fed with a high-fat diet with or with supplementation with a maple syrup extract (MSX). The MSX extract is prepared as described above with the use of a food-grade approved resin XAD-16 to prepare a food grade approved extract from maple syrup. The MSX extract is prepared from 50 L of maple syrup. The experimental groups are defined in Table 6 below:

TABLE 6

Experimental groups and respective diets

| Group | Diet |
| --- | --- |
| LFD | 10%-fat diet |
| 45F | 45%-fat diet |
| 45F + 0.06 MSX | 45%-fat diet with 0.06% MSX |
| 45F + 0.12 MSX | 45%-fat diet with 0.12% MSX |

LFD = low fat diet;
45F = high fat diet

Figure 25:
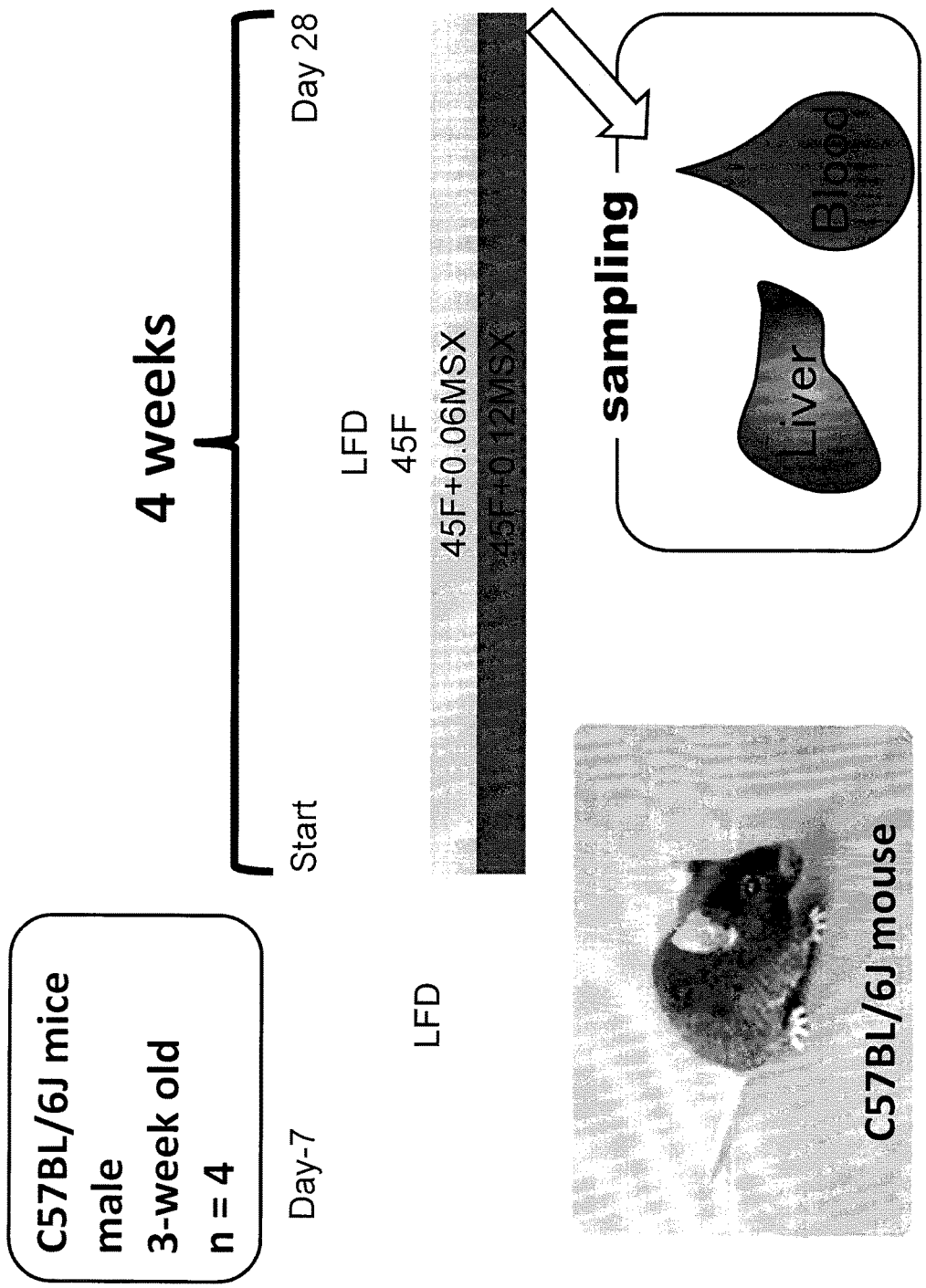
FIG. 25 illustrates the experimental design of a study described herein.
Figure 26:
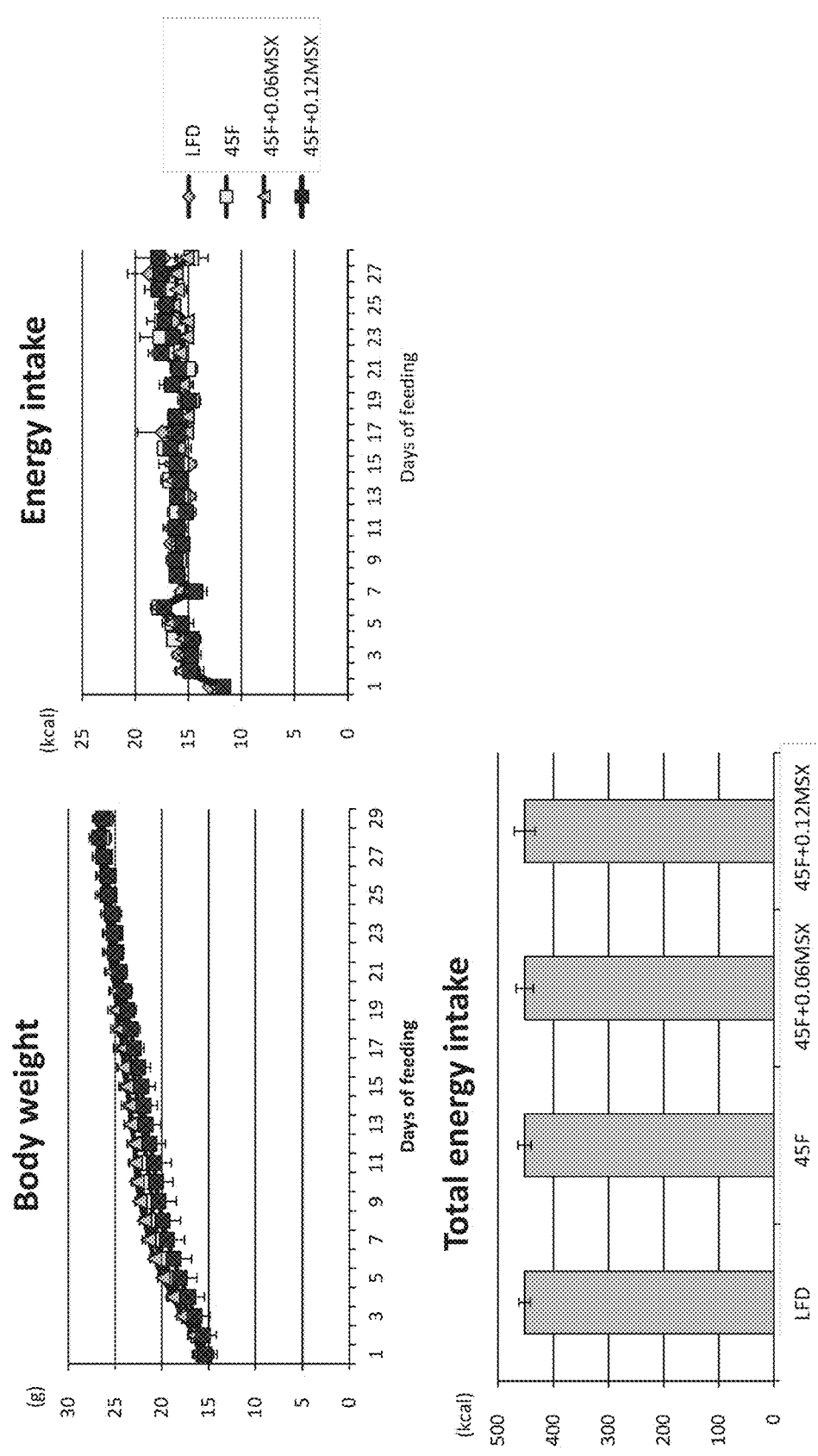
FIG. 26 illustrates experimental results of a study described herein.

As shown in FIG. 25, 3-week old C57/BL/6J male mice (N=4 in each group) are fed a low fat diet for 7 days, and then each group is switched to their respective experimental diet for 4 weeks (28 days). Liver and blood samples are collected at the end of the 4 week period. The results in FIG. 26 show that body weight increase and energy intake are the same between all 4 experimental groups.

Figure 27:
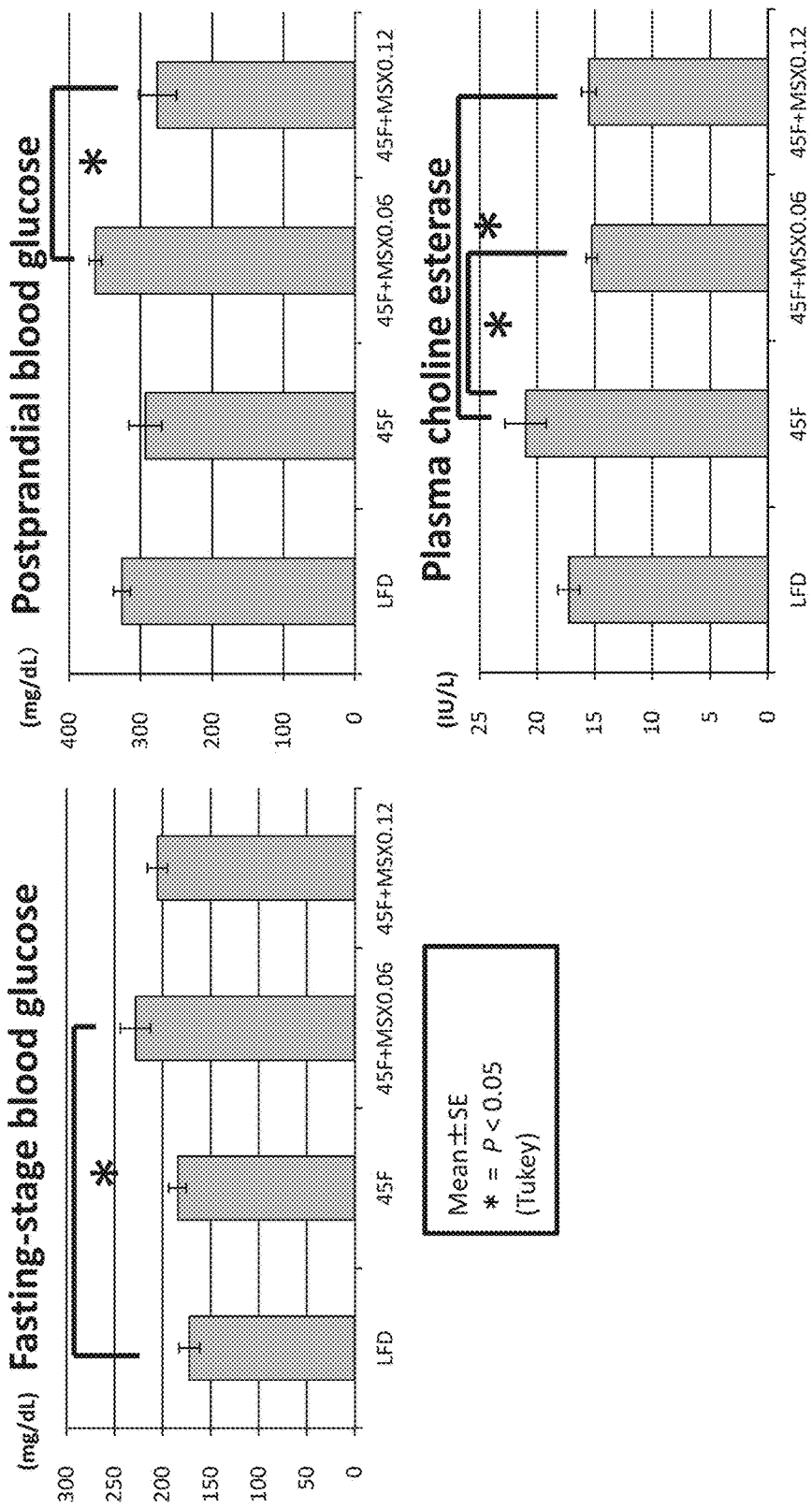
FIG. 27 illustrates experimental results of a study described herein.
Figure 28:
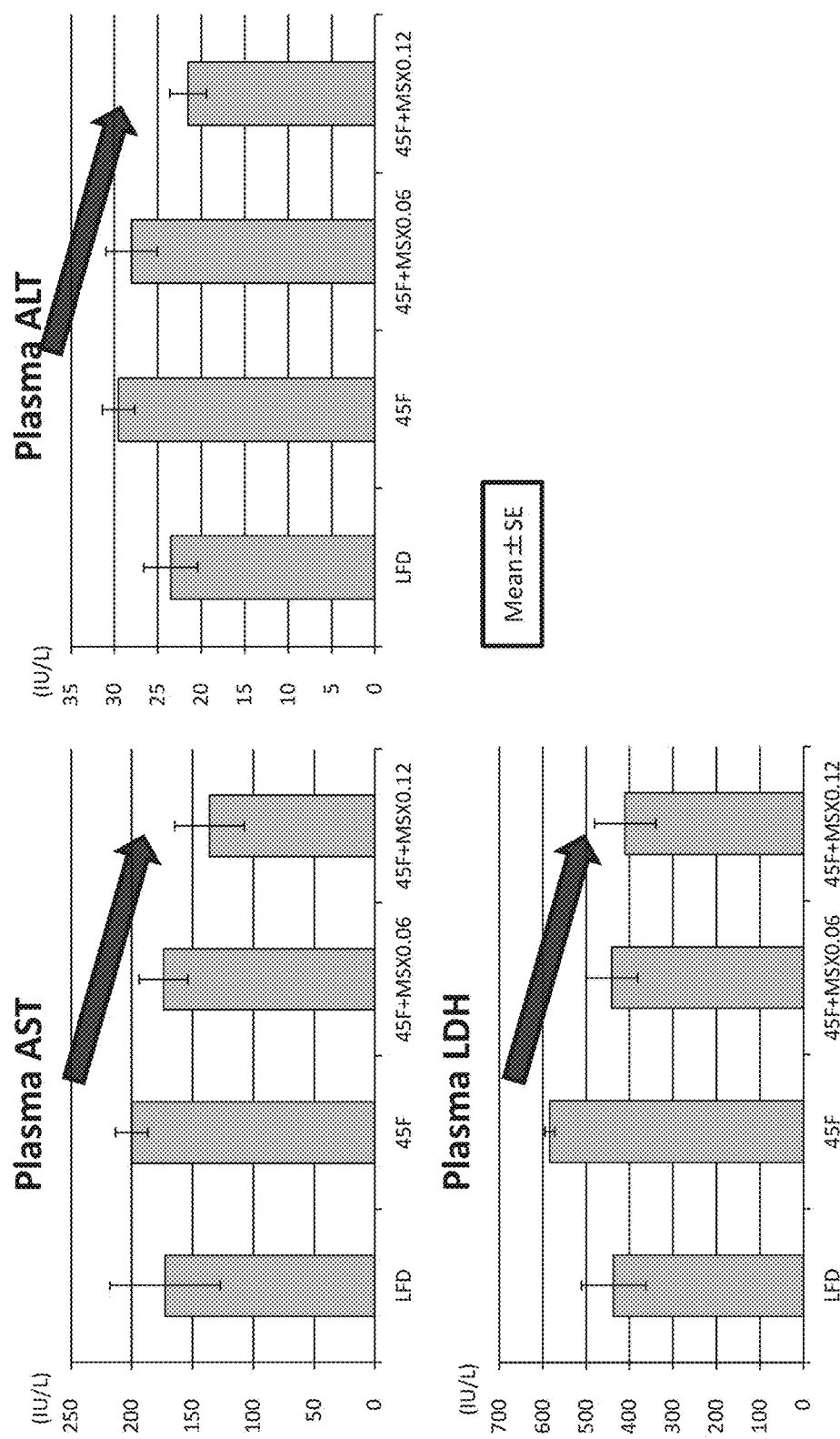
FIG. 28 illustrates experimental results of a study described herein.

However, as shown in FIG. 27, the level of plasma choline esterase is significantly decreased in animals treated with MSX. As shown in FIG. 28, the level of plasma AST, ALT and LDH all decrease in a dose dependent manner in the MSX treated groups, suggesting that MSX has a liver protecting effect, and that the liver-protecting factors are present in MSX.

Figure 29:
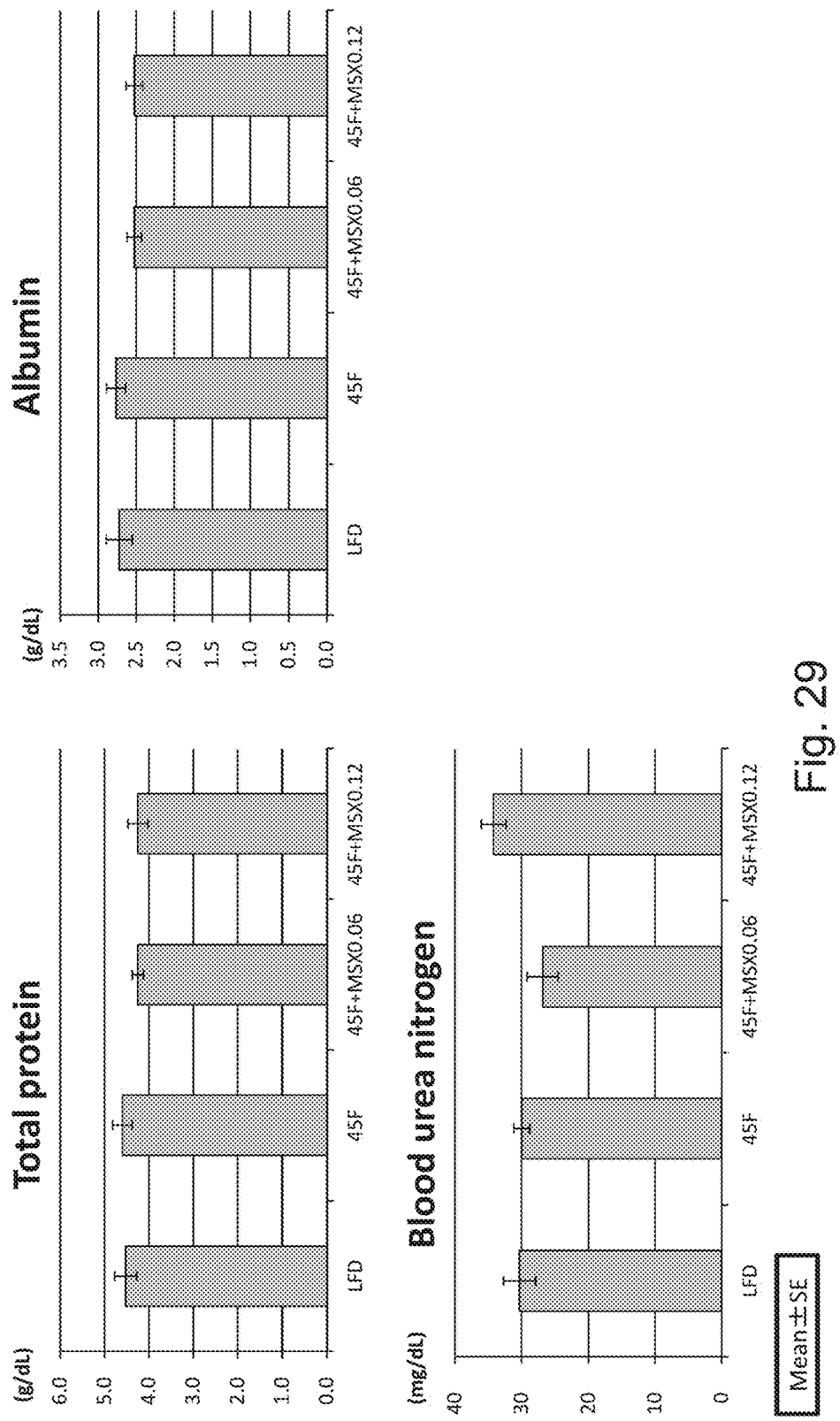
FIG. 29 illustrates experimental results of a study described herein.
Figure 30:
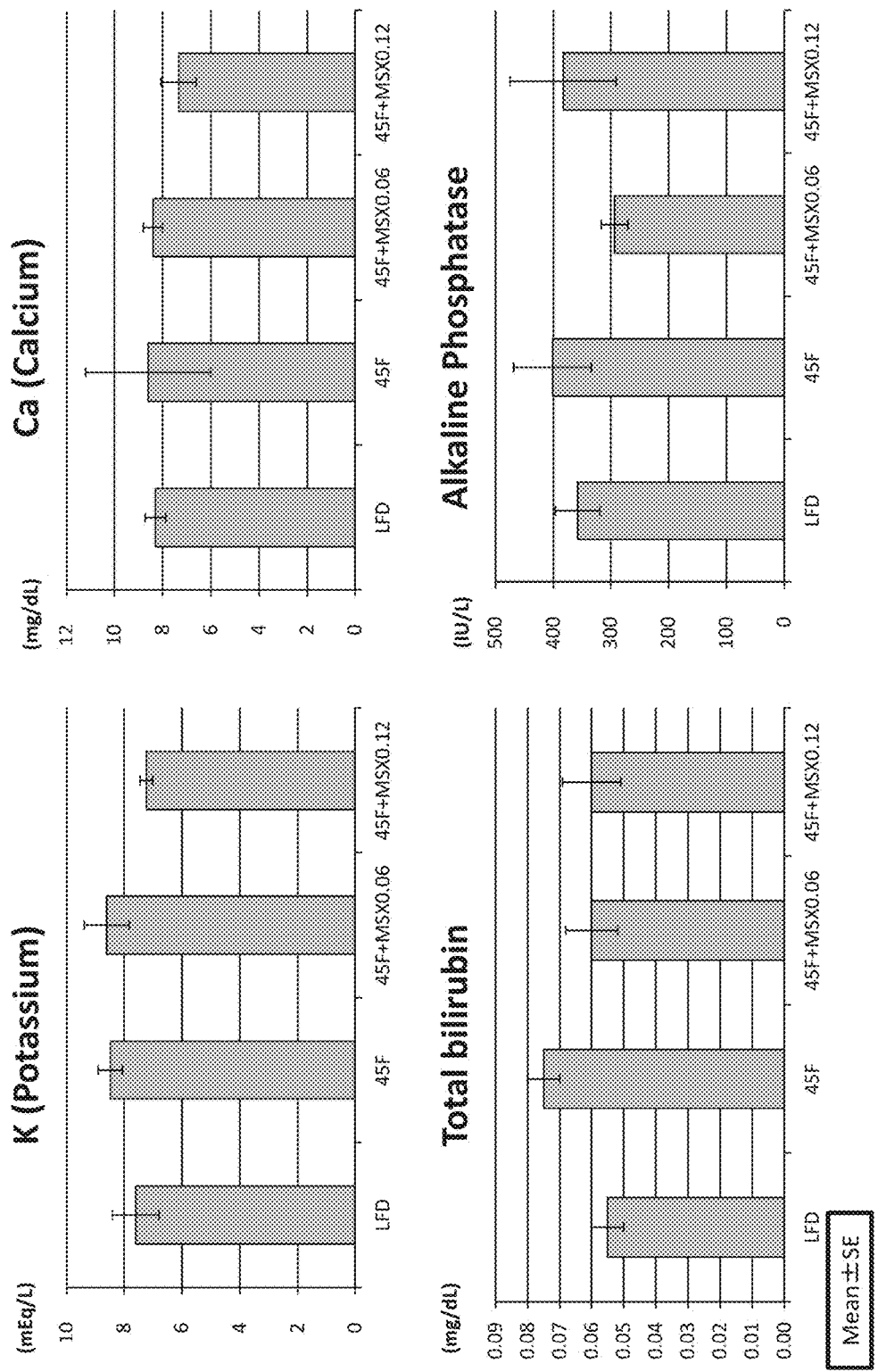
FIG. 30 illustrates experimental results of a study described herein.
Figure 31:
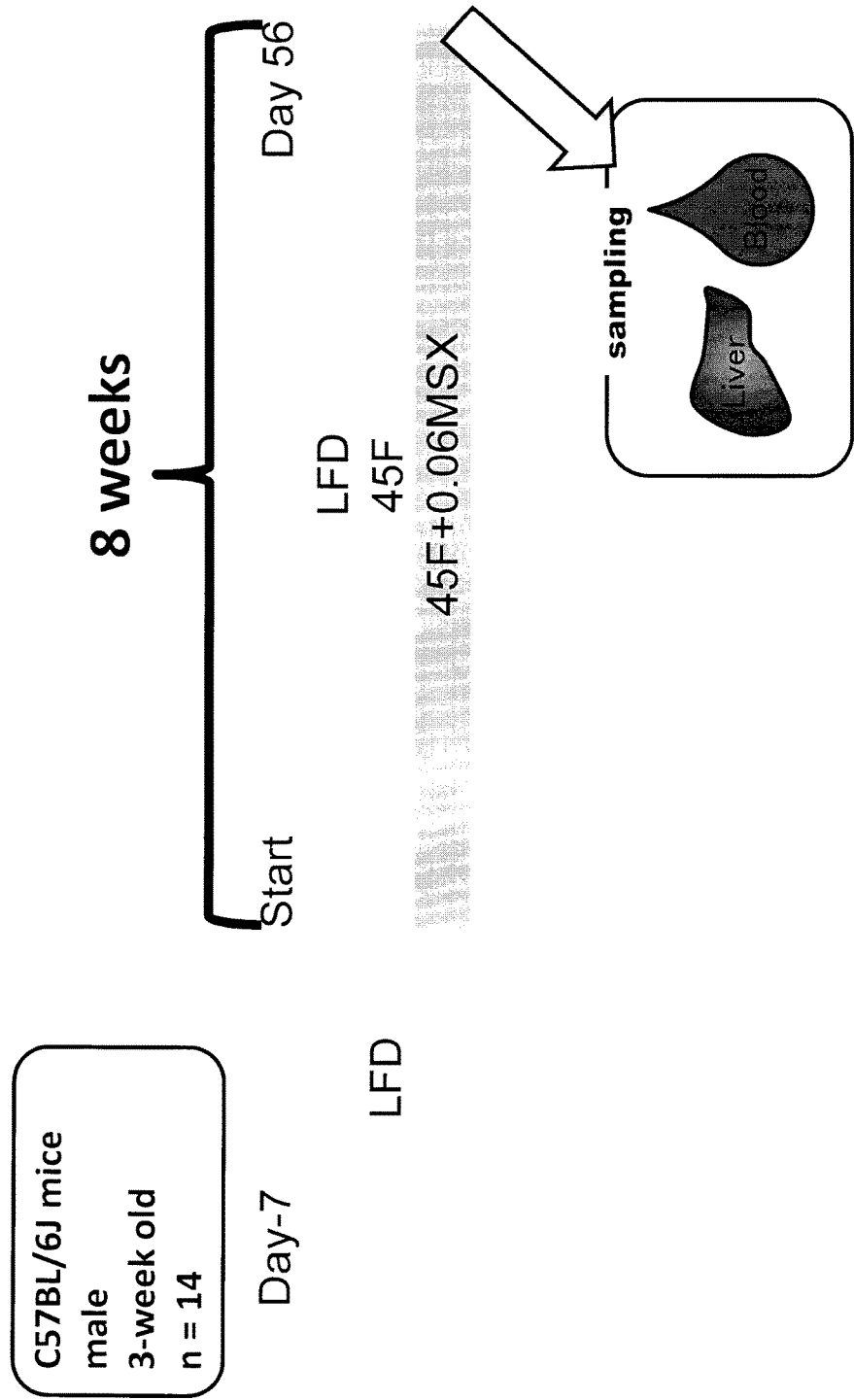
FIG. 31 illustrates the experimental design of a future study.

As shown in FIG. 29, the total plasma protein levels, albumin levels are approximately unchanged between each group, and the blood urea nitrogen levels appears slightly higher in the 0.12% MSX group. As shown in FIG. 30, total plasma potassium, calcium levels, total bilirubin and alkaline phosphatase levels do appears to trend toward the low fat diet levels in the 0.12% MSX group. And the total bilirubin level do appear to trend downward toward the low fat diet levels for each MSX treated group. In conclusion, there results show that the choline esterase levels are significantly decreased in the MST diet groups, and that AST, ALT and LDH levels are decreased in a dose dependent manner in the MSX diet groups. These results indicate that MSX has a liver protecting effects. To confirm these results, a new experiment is being carried out, in which experimental groups of each n=14 animals are being treated with low fat diet, a high fat diet, or a high fat diet supplemented with 0.6% MSX for a total of 8 weeks.

Example 4

Preparation of Preparation of a Food-Grade Approved Extract from Maple Syrup

Described is the methodology for the extraction of bioactive compounds from maple syrup without the sugar moiety, using two types of resin 1) FPX 66 and 2) XAD-16. These two resins both are divinylbenzene phases. The mechanism of adsorption of polyphenols on these phases is exclusively by means of hydrophobic interactions.

Methodology:
1. Dilution of a 5 L (6 kg) portion of maple syrup with 2.1 L of deionized water.
2. Adsorption of the maple syrup mixture on 16.8 kg of wet Amberlite™ FPX66 or XAD-16 (5.0-6.7 kg dry mass) for 16 hours.
3. Wash of the column with deionized water (7×15 L).
4. Elution with denatured ethanol (3×15 L). Before each elution, let the ethanol in contact with the resin for 30 minutes.
5. Evaporation of ethanol on "rotary evaporator". The temperature of the water bath is set from 37° C. and does not exceed 40° C.
6. Isolation of the MSX fraction (15.3 g).
7. Reconditioning of the resin with two portions of 10 L of deionized water.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A composition having liver protecting effects consisting essentially of about 0.06% to about 0.12% of a maple syrup extract which has been prepared using a styrene divinylbenzene copolymer resin and about 99.94% to about 99.88% of a carrier selected from the group consisting of a coating on a dietary supplement, a protein rich drink, and an energy drink, wherein the carrier and the maple syrup extract are not the same.

* * * * *